(12) United States Patent
Dietz et al.

(10) Patent No.: US 7,959,555 B2
(45) Date of Patent: Jun. 14, 2011

(54) METHOD AND DEVICE FOR DEPLOYMENT OF A SUB-PERICARDIAL SACK

(75) Inventors: Timothy G. Dietz, Terrace Park, OH (US); Eugene L. Timperman, Cincinnati, OH (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 12/578,280

(22) Filed: Oct. 13, 2009

(65) Prior Publication Data

US 2010/0036194 A1 Feb. 11, 2010

Related U.S. Application Data

(62) Division of application No. 11/141,116, filed on May 31, 2005, now Pat. No. 7,621,866.

(51) Int. Cl.
*A61F 2/00* (2006.01)
(52) U.S. Cl. ......................................................... 600/37
(58) Field of Classification Search ............... 600/16, 600/37; 128/897–898; 601/116, 119, 129, 601/151, 153; 604/48, 57, 59; 606/108, 606/139, 140, 141, 144, 151; 623/3.1, 909, 623/922
See application file for complete search history.

(56) References Cited

U.S. PATENT DOCUMENTS

| | | | |
|---|---|---|---|
| 5,256,132 A | 10/1993 | Snyders | |
| 5,337,754 A | 8/1994 | Heaven et al. | |
| 5,465,731 A | 11/1995 | Bell et al. | |
| 5,524,633 A | 6/1996 | Heaven et al. | |
| 5,647,372 A | 7/1997 | Tovey et al. | |
| 5,961,440 A | 10/1999 | Schweich, Jr. et al. | |
| 5,971,995 A | 10/1999 | Rousseau | |
| 6,045,497 A | 4/2000 | Schweich, Jr. et al. | |
| 6,050,936 A | 4/2000 | Schweich, Jr. et al. | |
| 6,059,715 A | 5/2000 | Schweich, Jr. et al. | |
| 6,077,214 A | 6/2000 | Mortier et al. | |
| 6,085,754 A | 7/2000 | Alferness et al. | |
| 6,123,662 A | 9/2000 | Alferness et al. | |
| 6,126,590 A | 10/2000 | Alferness | |
| 6,155,972 A | 12/2000 | Nauertz et al. | |
| 6,162,168 A | 12/2000 | Schweich, Jr. et al. | |
| 6,165,119 A | 12/2000 | Schweich, Jr. et al. | |

(Continued)

OTHER PUBLICATIONS

Lendlein, Andreas et al., "Shape-Memory Polymers", Angewandte Chemie International Edition (2002), vol. 41, pp. 2034-2057.

*Primary Examiner* — John P Lacyk
(74) *Attorney, Agent, or Firm* — Scully, Scott, Murphy & Presser, P.C.

(57) ABSTRACT

Various methods and devices for deploying a sub-pericardial sack about at least a portion of a heart to alleviate congestive heart failure. A medical device housing the sub-pericardial sack is inserted into the pericardial sack. An inverted umbrella framework is deployed through the medical device and into the pericardial sack to position the sub-pericardial sack adjacent the heart. The umbrella framework is then retracted through the medical device once the cardiac assist device is placed adjacent the heart. A steerable catheter can instead be deployed through the pericardial sack to deploy and position a cardiac assist device, such as a mesh, around the heart. The steerable catheter is covered by a sheath housing the cardiac assist device. Once the sheath is pulled back, the cardiac assist device is deployed and secured adjacent the heart. Filaments or tensions wires are used to tighten the mesh around the heart.

7 Claims, 31 Drawing Sheets

U.S. PATENT DOCUMENTS

| | | |
|---|---|---|
| 6,165,120 A | 12/2000 | Schweich, Jr. et al. |
| 6,165,121 A | 12/2000 | Alferness |
| 6,165,122 A | 12/2000 | Alferness |
| 6,169,922 B1 | 1/2001 | Alferness et al. |
| 6,174,279 B1 | 1/2001 | Girard |
| 6,179,791 B1 | 1/2001 | Krueger |
| 6,183,411 B1 | 2/2001 | Mortier et al. |
| 6,193,648 B1 | 2/2001 | Krueger |
| 6,230,714 B1 | 5/2001 | Alferness et al. |
| 6,241,654 B1 | 6/2001 | Alferness |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,293,906 B1 | 9/2001 | Vanden Hoek et al. |
| 6,332,863 B1 | 12/2001 | Schweich, Jr. et al. |
| 6,332,864 B1 | 12/2001 | Schweich, Jr. et al. |
| 6,332,893 B1 | 12/2001 | Mortier et al. |
| 6,370,429 B1 | 4/2002 | Alferness et al. |
| 6,375,608 B1 | 4/2002 | Alferness |
| 6,390,976 B1 | 5/2002 | Spence et al. |
| 6,402,679 B1 | 6/2002 | Mortier et al. |
| 6,402,680 B2 | 6/2002 | Mortier et al. |
| 6,406,420 B1 | 6/2002 | McCarthy et al. |
| 6,409,733 B1 | 6/2002 | Conlon et al. |
| 6,416,459 B1 | 7/2002 | Haindl |
| 6,425,856 B1 | 7/2002 | Shapland et al. |
| 6,482,146 B1 | 11/2002 | Alferness et al. |
| 6,494,211 B1 | 12/2002 | Boyd et al. |
| 6,514,194 B2 | 2/2003 | Schweich, Jr. et al. |
| 6,537,198 B1 | 3/2003 | Vidlund et al. |
| 6,537,203 B1 | 3/2003 | Alferness et al. |
| 6,544,168 B2 | 4/2003 | Alferness |
| 6,564,094 B2 | 5/2003 | Alferness et al. |
| 6,567,699 B2 | 5/2003 | Alferness et al. |
| 6,572,533 B1 | 6/2003 | Shapland et al. |
| 6,575,921 B2 | 6/2003 | Vanden Hoek et al. |
| 6,579,226 B2 | 6/2003 | Vanden Hoek et al. |
| 6,582,355 B2 | 6/2003 | Alferness et al. |
| 6,589,160 B2 | 7/2003 | Schweich, Jr. et al. |
| 6,612,979 B2 | 9/2003 | Lau et al. |
| 6,616,684 B1 | 9/2003 | Vidlund et al. |
| 6,620,095 B2 | 9/2003 | Taheri |
| 6,622,730 B2 | 9/2003 | Ekvall et al. |
| 6,629,921 B1 | 10/2003 | Schweich, Jr. et al. |
| 6,645,139 B2 | 11/2003 | Haindl |
| 6,673,009 B1 | 1/2004 | Vanden Hoek et al. |
| 6,695,769 B2 | 2/2004 | French et al. |
| 6,702,732 B1 | 3/2004 | Lau et al. |
| 6,755,779 B2 | 6/2004 | Vanden Hoek et al. |
| 7,291,105 B2 | 11/2007 | Lau et al. |
| 7,572,219 B2 * | 8/2009 | Lau et al. ................ 600/37 |
| 2002/0019580 A1 | 2/2002 | Lau et al. |
| 2002/0028981 A1 | 3/2002 | Lau et al. |
| 2002/0068850 A1 | 6/2002 | Vanden Hoek et al. |
| 2003/0004396 A1 | 1/2003 | Vanden Hock et al. |
| 2003/0078456 A1 | 4/2003 | Yilmaz et al. |
| 2004/0171906 A1 | 9/2004 | Lau et al. |
| 2004/0171909 A1 | 9/2004 | Alferness |
| 2004/0186342 A1 | 9/2004 | Vanden Hock et al. |
| 2004/0210104 A1 | 10/2004 | Lau et al. |
| 2005/0049611 A1 | 3/2005 | Lau et al. |
| 2006/0009675 A1 | 1/2006 | Meyer |

* cited by examiner

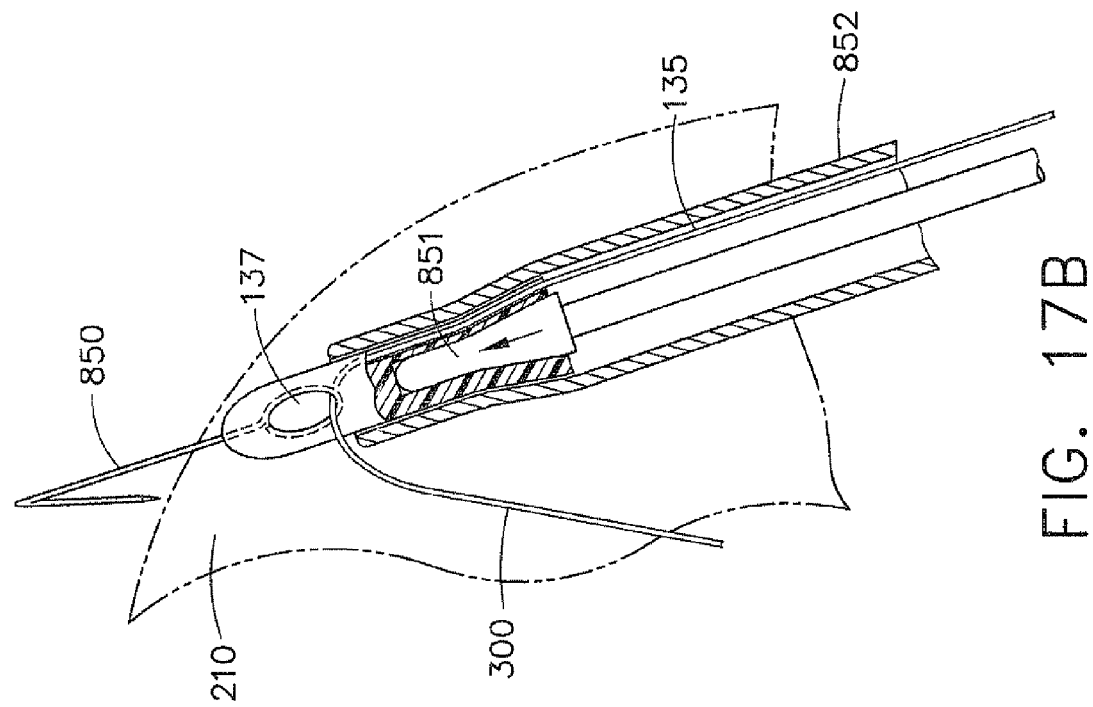
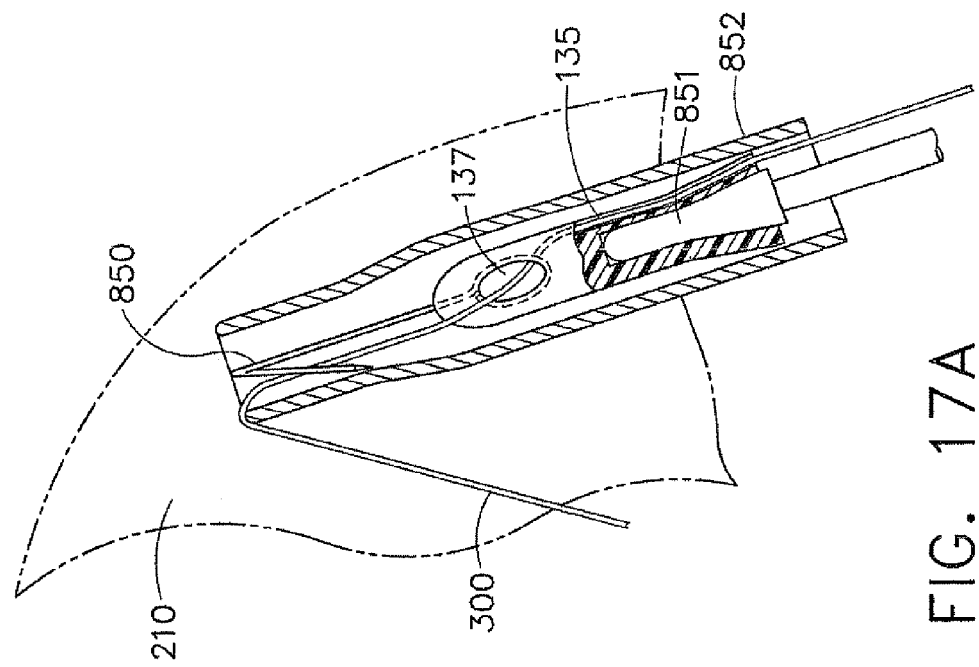

METHOD AND DEVICE FOR DEPLOYMENT OF A SUB-PERICARDIAL SACK

CROSS-REFERENCE TO RELATED APPLICATION

The present application is a continuation application of U.S. Ser. No. 11/141,116, filed May 31, 2005, the entire contents of which are incorporated herein by reference.

BACKGROUND OF THE INVENTION

1. Field of the Invention

This invention relates to methods and devices for treating congestive heart failure by deploying and tensioning a cardiac assist device about the heart. More specifically, this invention relates to methods and devices for deploying, positioning and tensioning a congestive heart failure passive restraint device adjacent the pericardium of the heart in a minimally invasive manner.

2. Prior Art

Heart failure syndrome is a highly debilitating and degenerative disorder resulting from damage to the heart muscle. The damage to the heart muscle may be caused by a number of conditions, including coronary artery disease, long standing hypertension, compromised heart valve(s) function, infection and diabetes.

Heart failure typically occurs when a weakened heart cannot pump an adequate amount of blood to meet the demands of the body's other organs and tissues. The defining characteristic in the progression of heart failure is that there is eventually a reduction of the heart's ability to meet the metabolic needs of the body.

Whatever the cause or source of damage, the heart's ability to pump adequate amounts of blood to support the body's needs is diminished, and the progressive deterioration of cardiac physiology and function begins. The inadequate supply of oxygen-rich blood often causes people with heart failure to experience shortness of breath and fatigue during even routine daily activities. As the condition progresses, the contraction rate of the heart increases in response to decreasing cardiac output. As a result, the chambers of the heart, particularly the ventricles of the heart, become increasingly enlarged as the heart tries to compensate for the inefficiencies. FIGS. 1a-1c show representative stages of progressive deterioration of a heart, wherein FIG. 1a shows a normal heart 10 with appropriately sized atrial chambers 1 and 2, and appropriately sized ventricular chambers 3 and 4, FIG. 1b shows slightly enlarged ventricular chambers 3 and 4, and FIG. 1c shows increasingly enlarged ventricular chambers 3 and 4. Ultimately, a complex process of damaging structural and functional changes to the heart results.

The disease of heart failure is common, lethal, and expensive to treat. An estimated 5.1 million Americans have heart failure with approximately 500,000 new cases diagnosed each year. In 1999, an estimated $20.3 billion in directs costs were spent for the care of heart failure patients. Heart failure is also the most common cause of hospitalization for patients 65 years and older in the United States. The mortality rate is 50% at five years for patients diagnosed with heart failure, and to date, there are limited treatment alternatives available.

Certain cardiac disease treatment devices have been proposed to help alleviate the disease of heart failure. For example, U.S. Pat. No. 6,425,856 provides a cardiac constraint device comprised of a jacket made of biologically compatible material. The jacket is configured to surround a valvular annulus of the heart and at least the ventricular lower extremities of the heart. FIG. 1d illustrates how the jacket 20 may be positioned around the heart 10 to improve cardiac function. The jacket works on a passive, mechanical level to reduce periodic myocardial over-stretch and wall stress, interrupts the angle of continual further expansion of the ventricular walls, and serves as a constant "reminder" to the heart of how it should perform. The jacket thus encourages down-regulation of increased local neurohormonal activity, and reduction or elimination of cardiomyocyte maladaptive gene expression.

These actions may halt the progressive deterioration of the heart and may stimulate reverse remodeling of the heart. Mechanisms responsible for remodeling of the heart are not singular and vary from patient to patient. For many patients, remodeling can occur through multiple mechanisms. Sometimes the individual mechanisms act synergistically to achieve an effect that exceeds the simple additive effect of non-interacting mechanisms.

Once positioned as desired around the heart, the jacket 20 is sutured to the heart. The deployment of a jacket is a method for deploying a material or structure that interrupts the cycle of heart failure. The minimum expectation would be to slow the progression of the disease; the preferred expectation would be the reduction of the disease (i.e., remodeling). The effect of the jacket can be on muscle cells, connective tissues, vascular tissues and enervation tissues. Ideal positioning of the jacket around the heart has proved problematic however, particularly where endoscopic tools and techniques are used. Other current procedures deploy the mesh through traditional open sternotomy procedures, which are very invasive.

An alternative procedure for surrounding a heart with a cardiac assist device proposes endoscopically placing a mesh underneath the heart and then pulling corners of the mesh sheet up and around the heart, as disclosed in co-pending U.S. patent application Ser. No. 10/881,510, filed Jun. 30, 2004, of common assignment herewith. Each corner of the mesh sheet is provided with suture tethers that are pulled in a designated sequence in order to wrap the mesh sheet around the heart.

Anatomically, as shown in FIG. 2, the pericardial sack 200 covers the heart 210 and connects to the veins 220 superiorly and to the diaphragm 230 inferiorly. It is possible to access the pericardial sack under the sternum 240, by dissecting just under the sternum. Conventionally, such access has been used to introduce drugs, growth factors, stem cells, etc., but not to help alleviate congestive heart failure or the conditions leading thereto.

Therefore, a need exists for methods and devices that deploy, position and tension a cardiac assist device around the pericardium of the heart in a relatively quick and minimally invasive manner.

SUMMARY OF THE INVENTION

Accordingly, various methods and devices for deploying a passive restraint mesh cardiac assist device into the pericardial space and adjacent the heart is provided by accessing the pericardial sack.

In some embodiments of the invention, the device and mesh are deployed by accessing the pericardial sack under the sternum. In other embodiments of the invention, the device and mesh are deployed elsewhere through the pericardial sack. Once deployed, the mesh is secured to the heart and helps alleviate CHF or the conditions leading thereto. Deployment of the mesh may be done fluoroscopically and the securing of the mesh may be done endoscopically to minimize the invasiveness of the procedures.

Accordingly, a method for positioning a cardiac assist device adjacent at least a portion of a heart is provided, the method comprising providing a delivery device comprising a handle, at least two elongate arms each having a proximal end and a distal end, at least the proximal end being disposed within the handle, and a first filament attached to a cardiac assist device and slidably attached to the distal end of the at least two elongate arms, positioning the at least two elongate arms adjacent at least a portion of a heart, and manipulating the filament to position the cardiac assist device from a first position, proximal the distal ends of the at least two elongate arms, to a second position, about at least a portion of the heart.

Further, a system for deploying a cardiac assist device on at least a portion of a heart is provided, the system comprising a hollow tubular instrument, the instrument having a proximal end and a distal end, at least two elongate arms movable between a first position substantially disposed within the hollow tubular instrument and a second position whereat at least the distal ends of the arms extend beyond the distal end of the instrument, and a cardiac assist device slidably attached to the at least two elongate arms, and movable between a proximate position whereat at least a portion of the jacket is disposed within the hollow instrument when the at least two elongate arms are in the second position, and a distal position, whereat the cardiac jacket is disposed outside the hollow instrument when the at least two elongate arms are in the second position.

Additionally, an apparatus for positioning a cardiac assist device adjacent at least a portion of a heart is provided, the apparatus comprising a hollow tubular instrument, the instrument having a proximal end and a distal end and a longitudinal axis, and at least two elongate arms movable from a first position within the instrument to a second position adjacent at least a portion of the heart, wherein each of said at least two elongate arms have a distal end biased to follow the contours of the heart as the elongate arms are deployed. The distal end of each elongate arms is thus comprised of a first portion curved outward relative to the longitudinal axis of the instrument; a second portion extending from the first portion and curved inwardly toward the longitudinal axis of the instrument; a third portion extending continuously from the second portion and curved outwardly from the longitudinal axis of the instrument, and a fourth portion extending continuously from the third portion and curved inwardly toward the longitudinal axis of the instrument, whereby the radius of curvature of each of the first, second, third and fourth portions contributes to the elongate fingers following the contours of the heart as the elongate arms are deployed.

Finally, a separate method for positioning a cardiac assist device adjacent at least a portion of a heart is provided, the method comprising creating an opening in the pericardium of a patient at a location other than proximate the apex of the heart, inserting a delivery device into the opening, delivering a cardiac assist device into the pericardial sack through the delivery device, and disposing the cardiac assist device about at least a portion of the heart.

The above and other features of the invention, including various novel details of construction and combinations of parts, will now be more particularly described with reference to the accompanying drawings and claims. It will be understood that the various exemplary embodiments of the invention described herein are shown by way of illustration only and not as a limitation thereof. The principles and features of this invention may be employed in various and numerous embodiments without departing from the scope of the invention.

BRIEF DESCRIPTION OF THE DRAWINGS

These and other features, aspects, and advantages of the apparatus and methods of the present invention will become better understood with regard to the following description, appended claims, and accompanying drawings where:

FIGS. 17a-17f illustrate another embodiment of deploying and securing a cardiac assist device to an intended portion of the heart according to the systems and methods of the invention.

DETAILED DESCRIPTION OF THE INVENTION

Figure 1C:
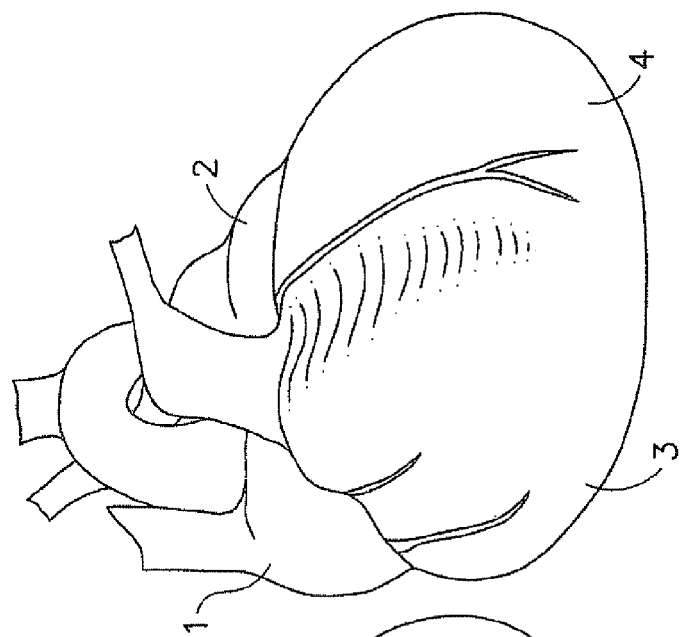
FIGS. 1a-1c illustrate progressive states of deterioration of a heart representative of heart failure conditions.
Figure 1B:
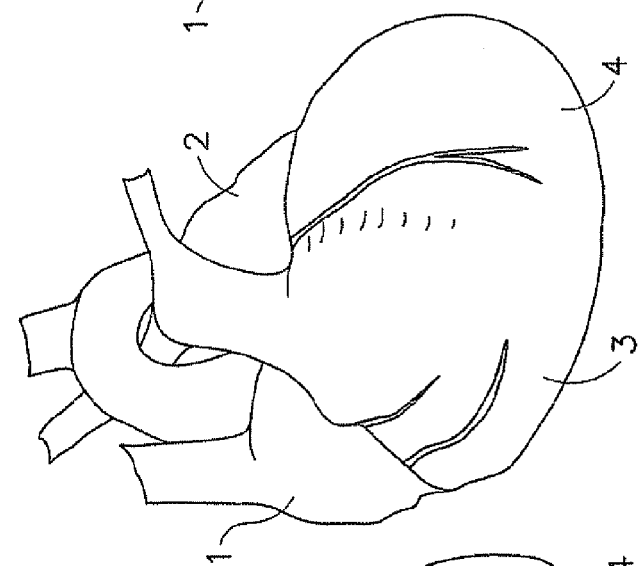
Figure 1A:
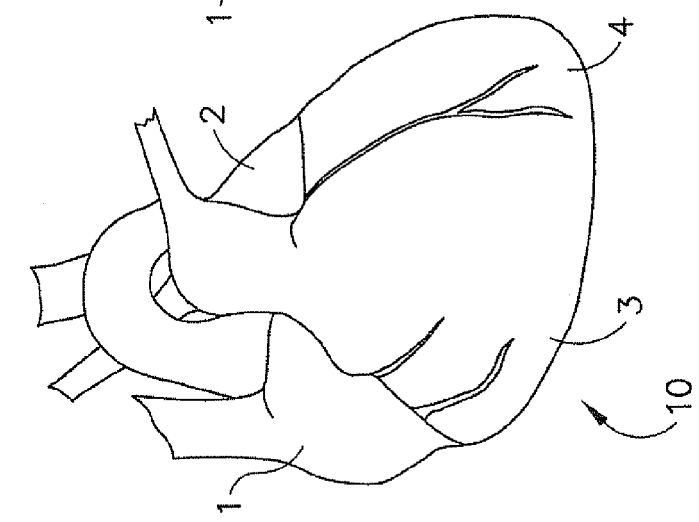
Figure 1D:
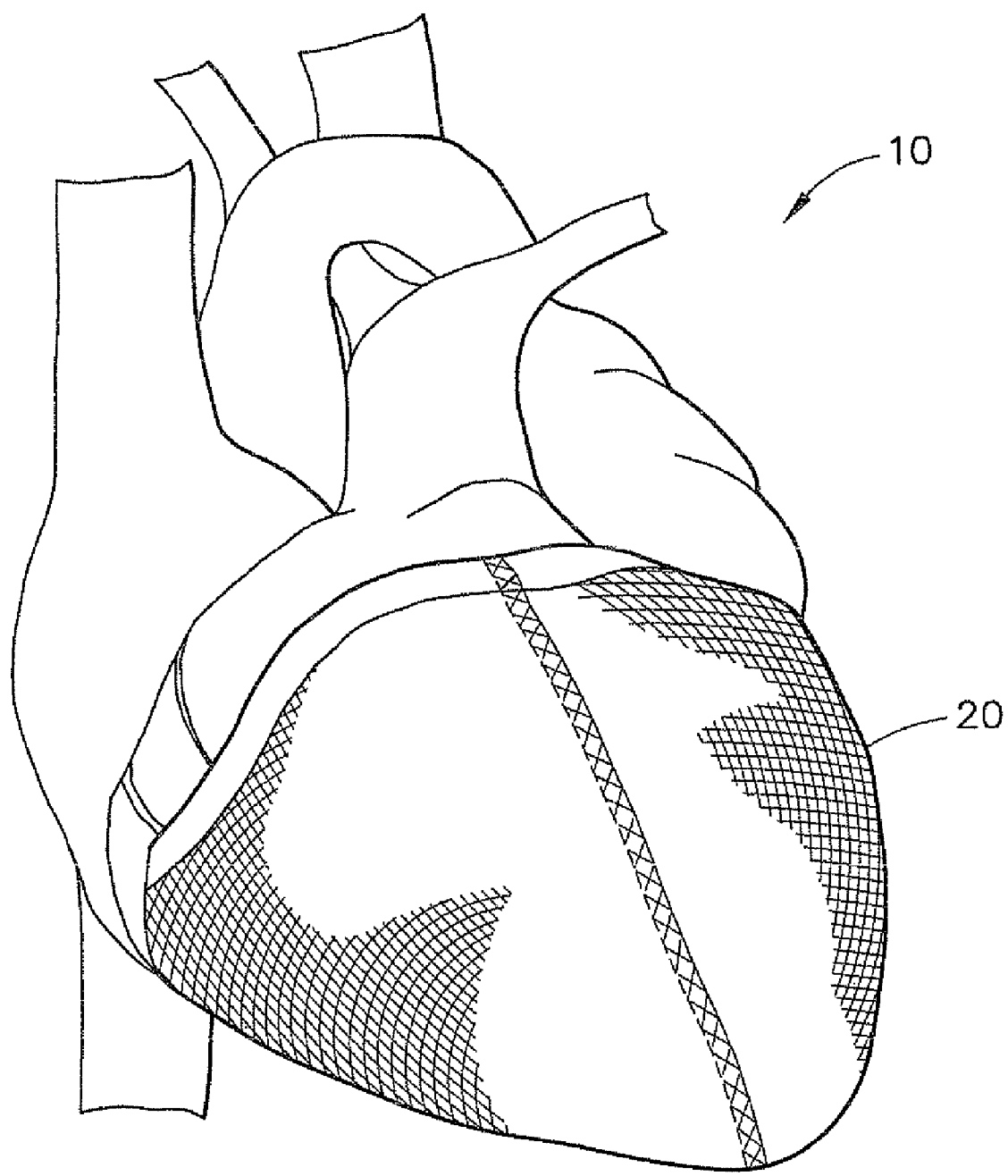
FIG. 1d illustrates a prior art mesh jacket placed around a heart.
Figure 2:
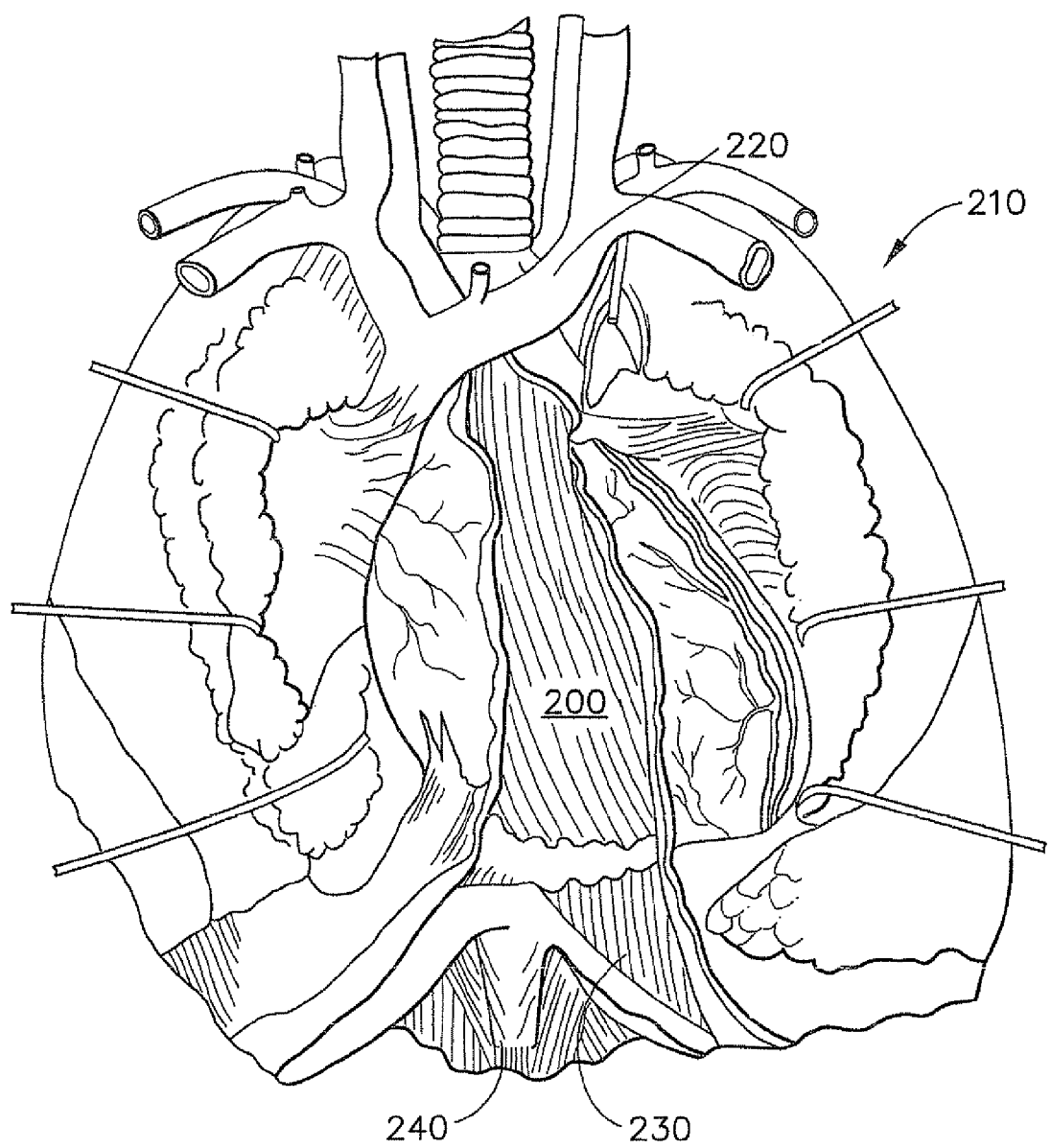
FIG. 2 illustrates the anatomy of a pericardial sack covering a heart.
Figure 3A:
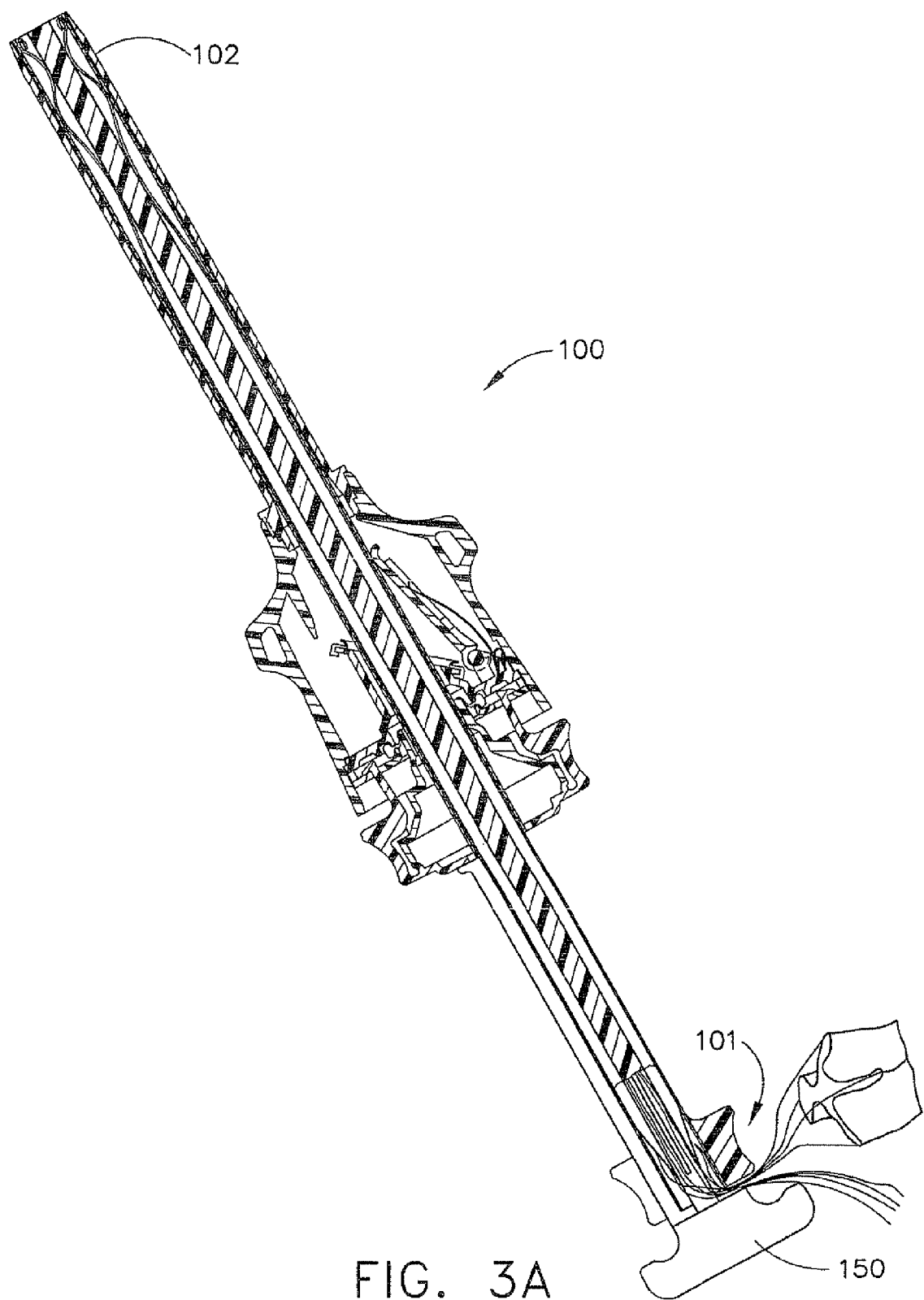
FIGS. 3(a) and 3(b) illustrate a device for delivering a jacket through a pericardial sack according the systems and methods of the invention.
Figure 3B:
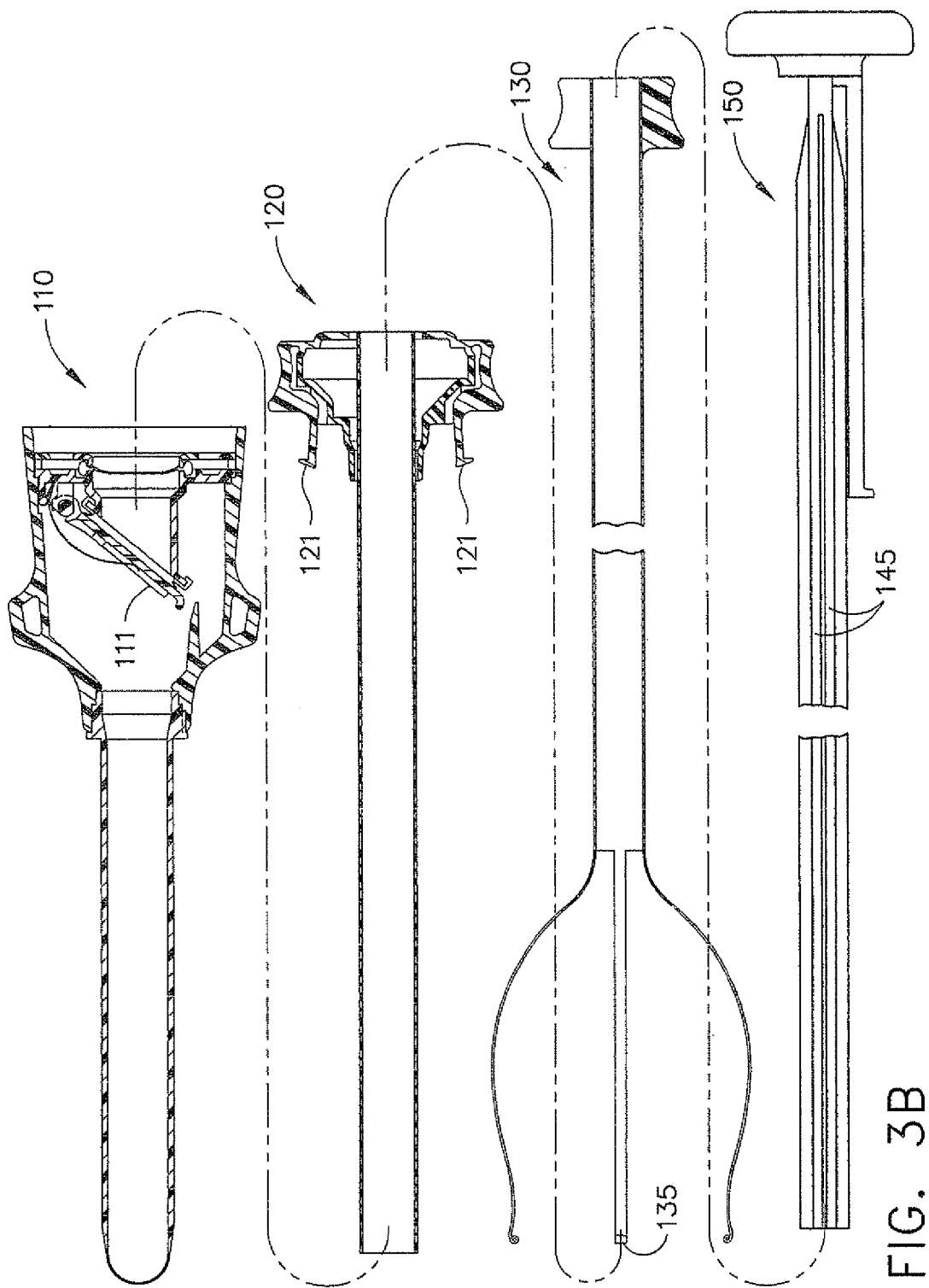
Figure 3C:
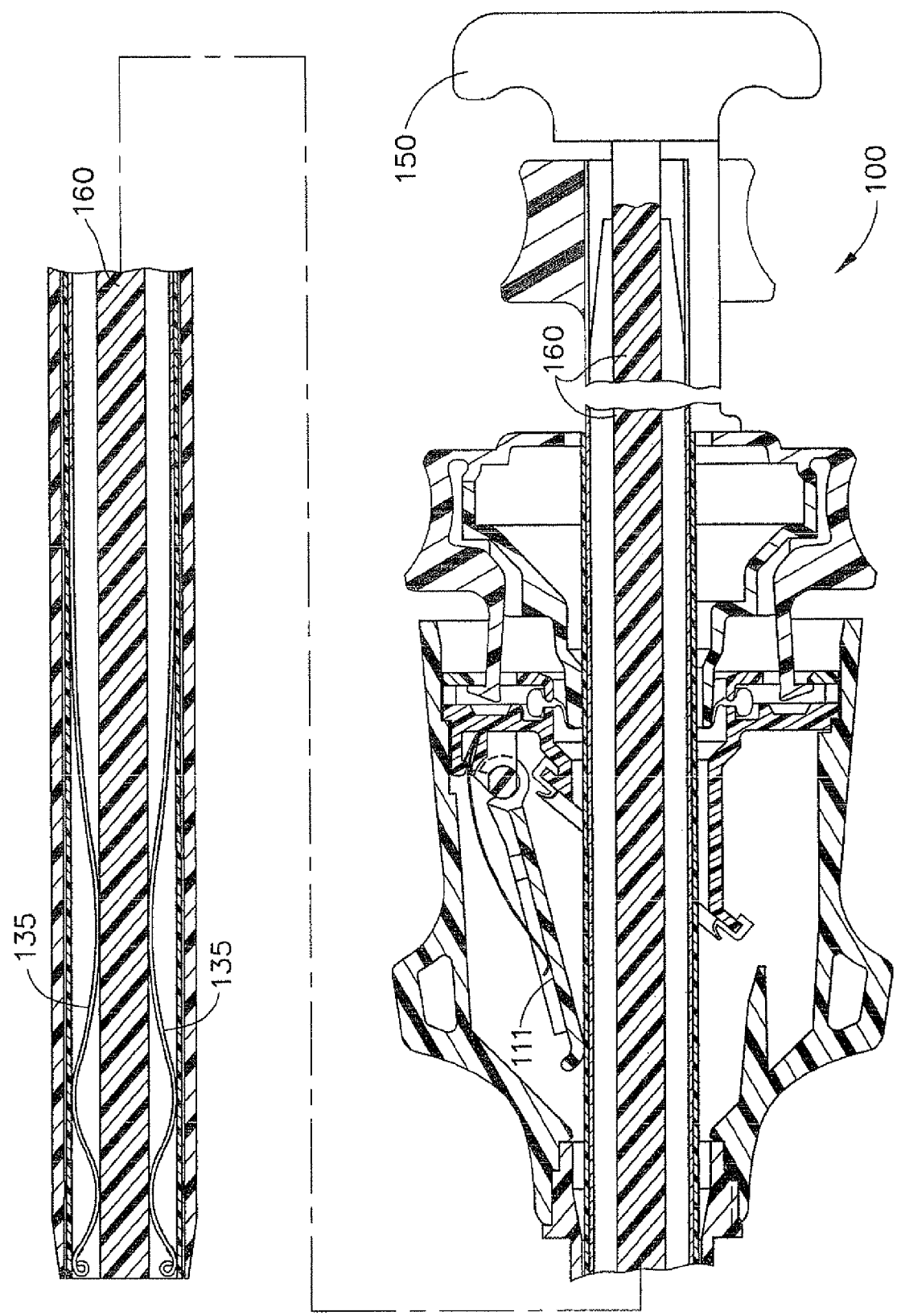
Figure 4A:
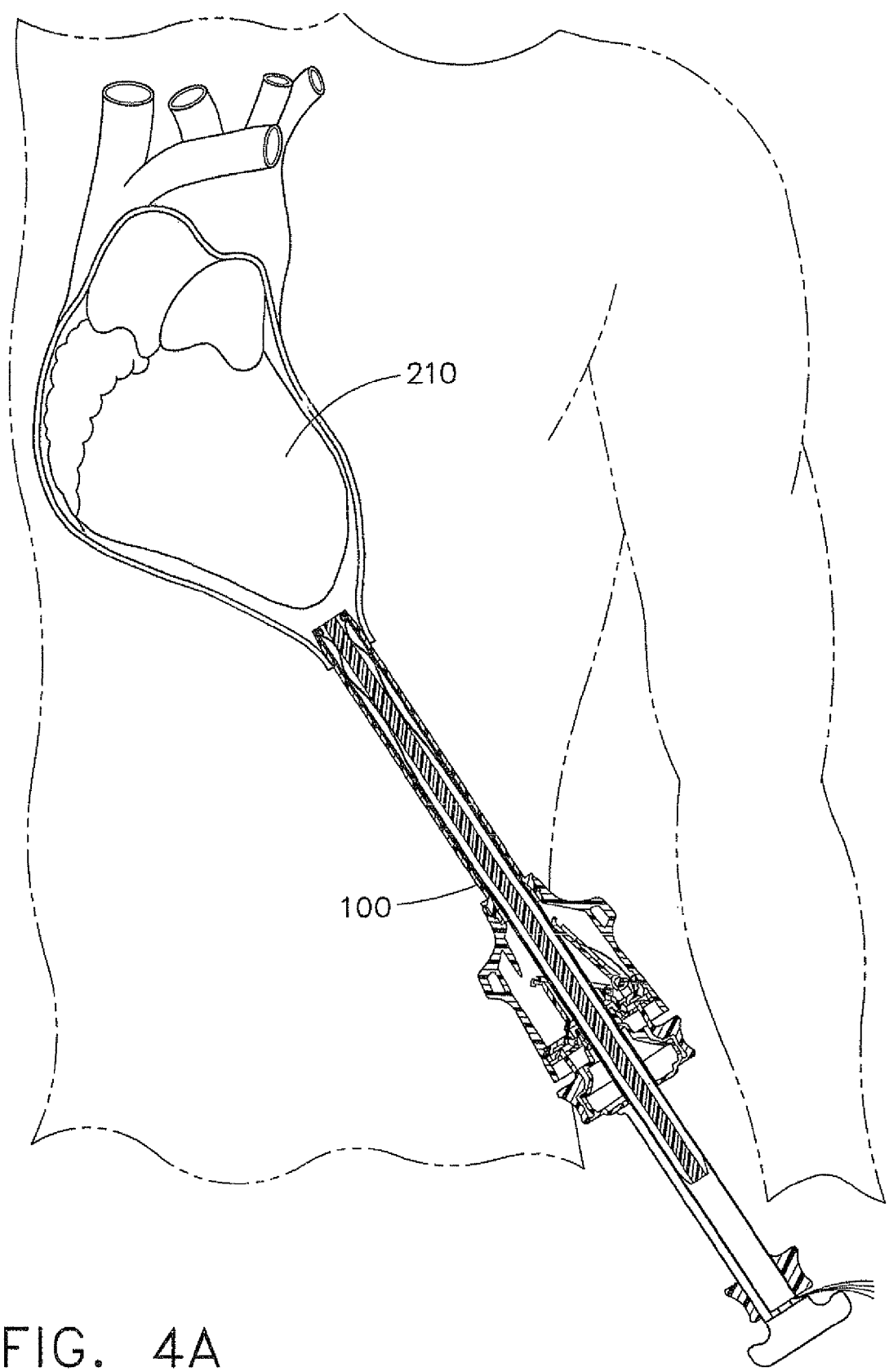
FIGS. 4-11 illustrate progressive deployment of the device of FIGS. 3a-b for deploying a jacket through the pericardial sack and about the heart according to a first embodiment of the present invention.
Figure 4B:
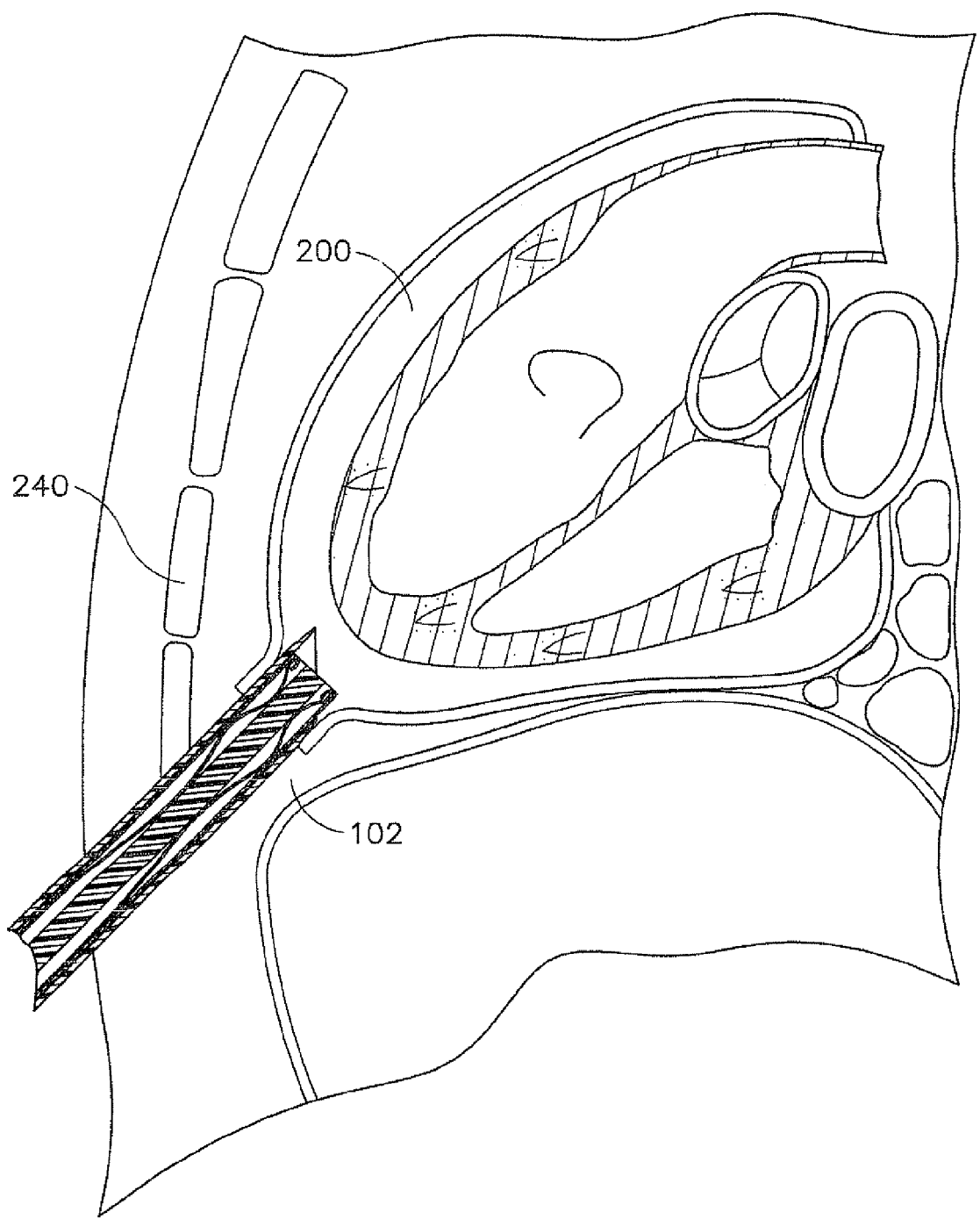

FIG. 3(a) shows a device 100 in accordance with a first embodiment of the systems and methods of the invention. The device 100 has a proximal end 101 and a distal end 102. The proximal end 101 is provided with a handle 150. FIG. 3(b) shows, in dissembled view, various components that comprise the device 100. FIG. 3(c) shows a partially assembled view of the device 100.

Referring to FIG. 3(b), the device 100 is comprised of outer trocar 110, tube 120, container tube 130 and device 140. The outer trocar 110 is a standard access instrument, with a valve 111 provided for insufflation. Tube 120 fits inside and latches onto the outer trocar 110 via retaining clips 121 in conventional manner. Containing tube 130 has elongate arms 135 extending therethrough. When assembled, the containing tube 130 fits inside the tube 120 that is latched onto the outer trocar 110. Finally, a device 140 fits inside the containing tube 130 and is provided with filaments 145 that are controlled by the handle 150 provided at an outer end of the device 140.

FIG. 3(c) shows a partially assembled view of the device 100, wherein a filament management means 160 is further provided throughout the device 100 to keep the elongate arms 135 oriented in the device 100 prior to deployment.

FIGS. 4-11 illustrate one embodiment of deploying a jacket 1000 as a passive restraint about a heart using the device 100 according to the invention. FIG. 4(a) shows the device 100 positioned to deliver a cardiac assist device adjacent to at least a portion of the heart 210. FIG. 4(b) is a close-up of FIG. 4(a) and shows, in greater detail, a distal end 102 of the device 100 gaining entry to the pericardial sack 200 just under the sternum 240.

Figure 5:
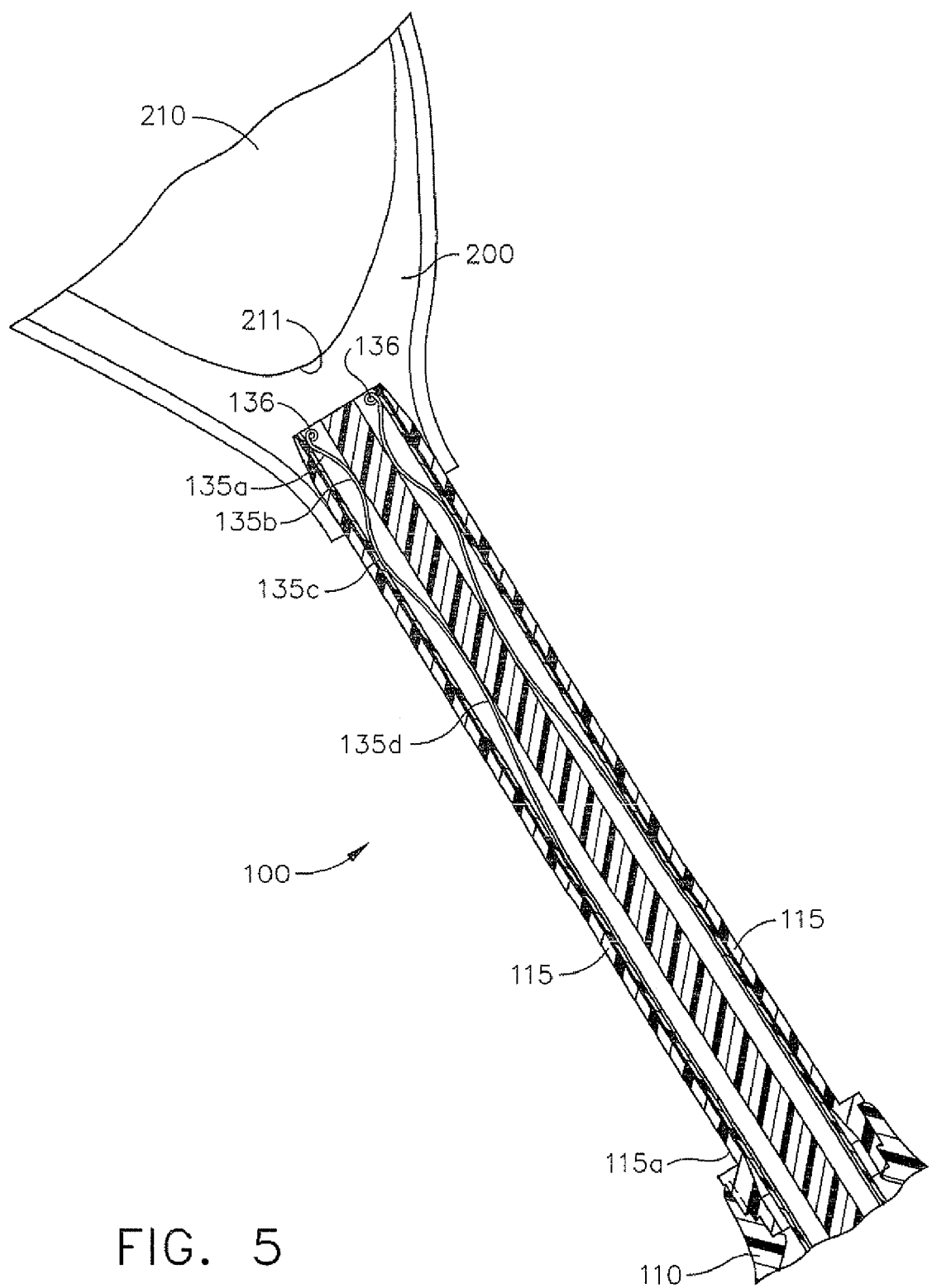
Figure 6:
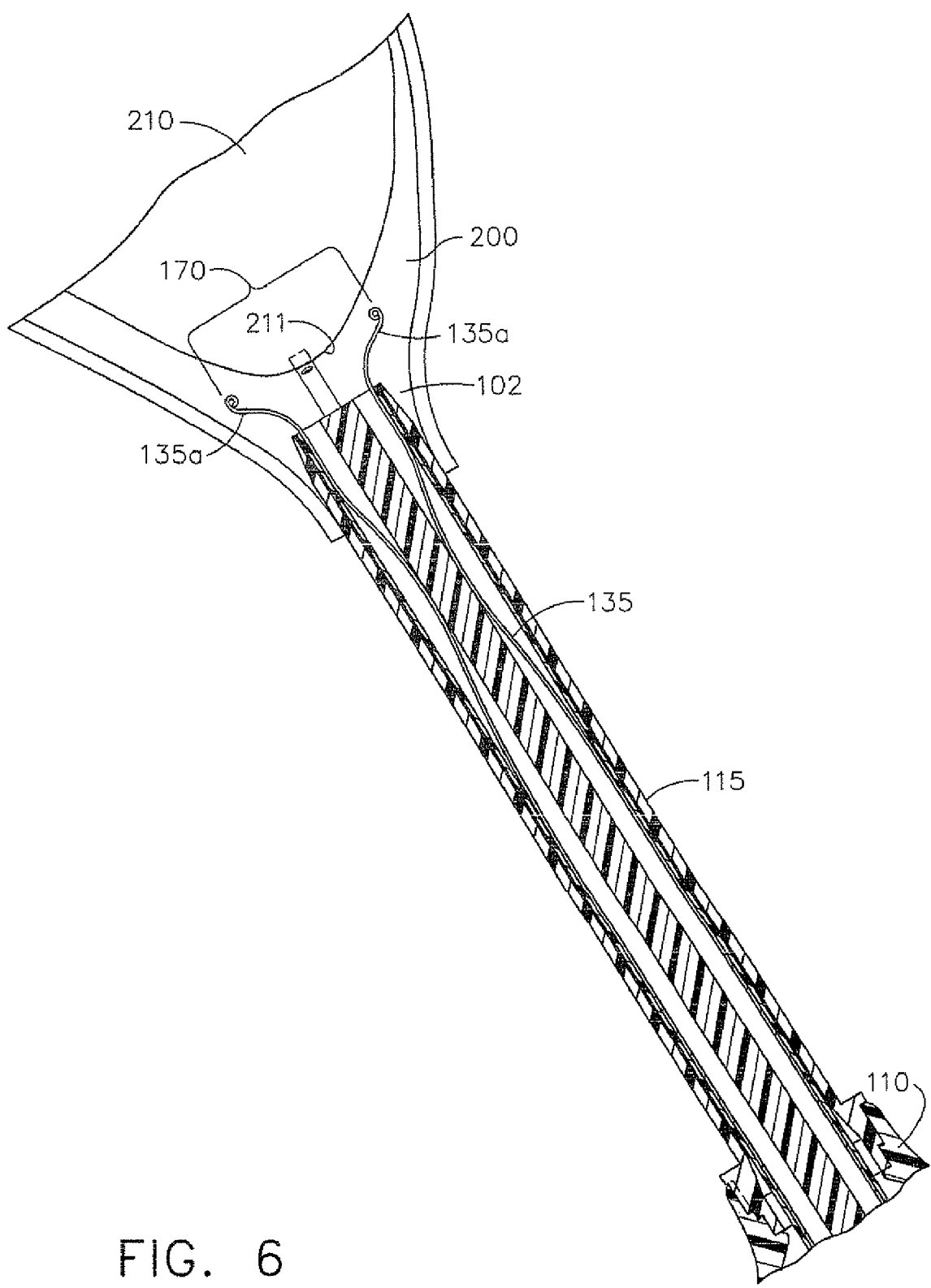
Figure 7:
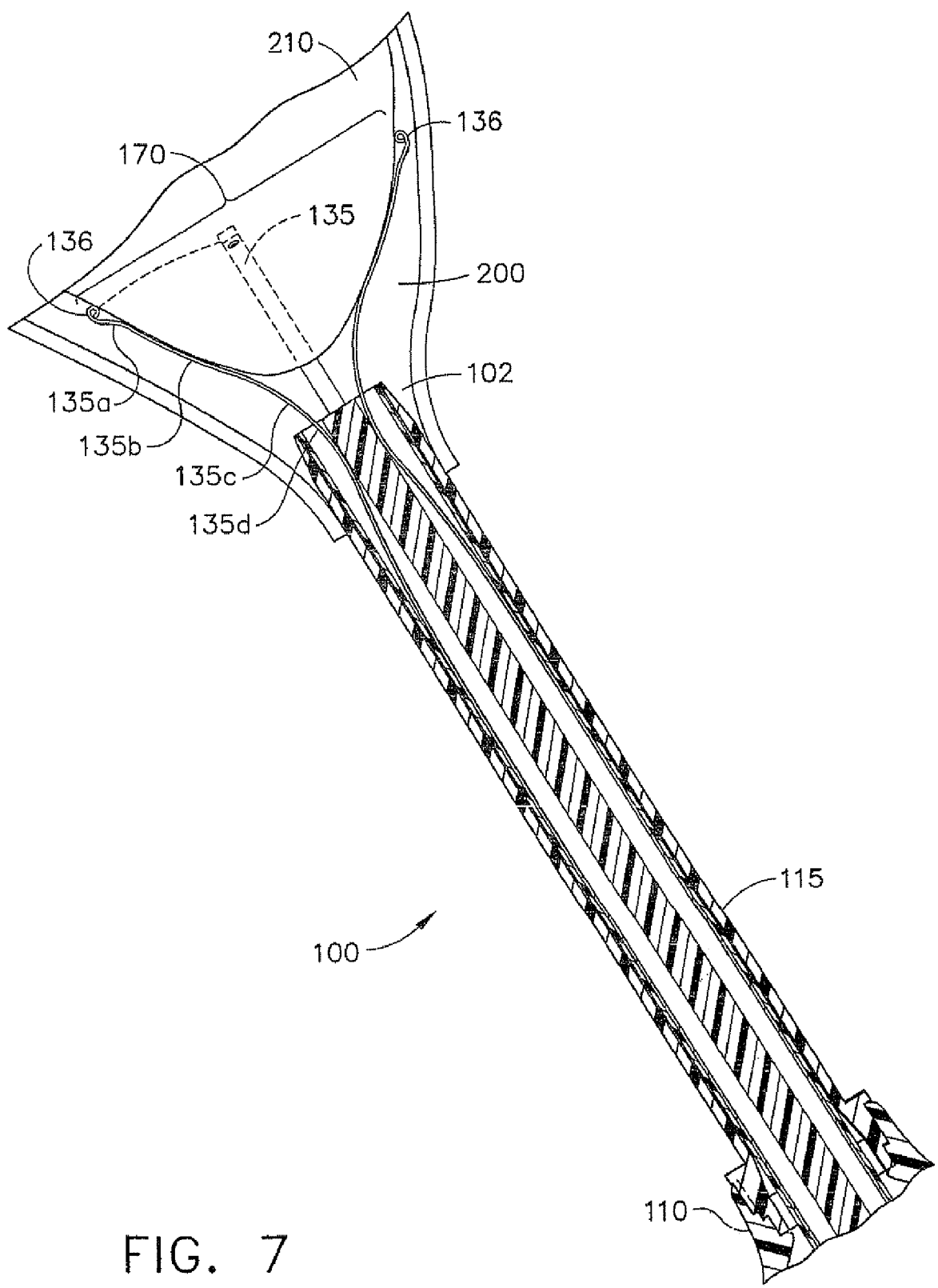
Figure 8:
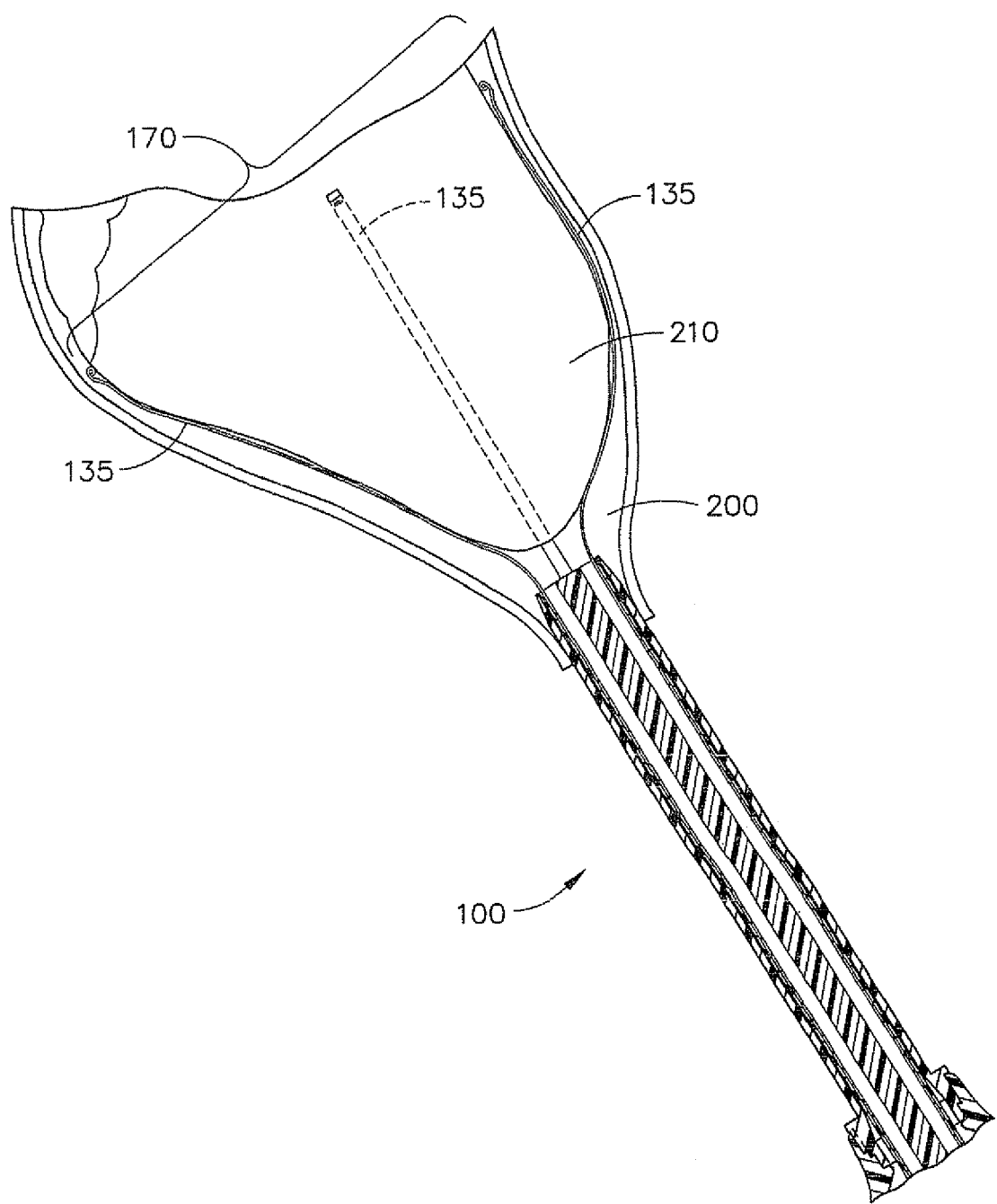

As shown in FIG. 5, the device 100 further comprises a trocar tube 115 extending from the outer trocar 110. The trocar tube 115 has a proximal end 115a closest to the outer trocar 110, and a distal end 115b opposite thereof. The distal end 115b of the trocar tube 115 generally corresponds to the distal end 102 of the device 100. The trocar tube 115 houses the elongate arms 135 that are slowly deployed out of the trocar tube 115 through the distal end 115b thereof, as shown in FIGS. 6-8. When fully deployed, the elongate arms 135 form an inverted umbrella 170, as shown in FIG. 7. The elongate arms 135 thus are comprised to be flexible enough to conform to the shape of the heart 210 when deployed but biased enough to maintain the intended inverted umbrella 170.

With respect to the elongate arms 135, the distal ends of the elongate arms are each comprised of a first portion 135a, a second portion 135b, a third portion 135c, and a fourth portion 135d. The first portion 135a contacts the surface of the heart 210 as the elongate arms 135 are deployed. The first portion 135a is curved outwardly from the longitudinal axis of the device 100. The second portion 135b extends continuously from the first portion 135a and is curved inwardly toward the longitudinal axis of the device 100. The third portion 135c then extends continuously from the second portion 135b and outwardly from the longitudinal axis of the device 100. The fourth portion 135d then extends continuously from the third portion and inwardly towards the longitudinal axis of the device 100. The radius of curvature of each portion 135a, 135b, 135c and 135d thus contributes to the elongate arms 135 following the contours of the heart as the elongate arms 135 are deployed. The first portion 135a, may further include a coiled tip 136 or other blunted tip so as to minimize damage to adjacent tissues as the elongate arms are deployed. Ideally, the lateral width across the elongate arms 135 is more than the thickness or depth of the elongate arms 135 towards the heart 210 so as to enable more flexibility in the elongate arms 135 towards and away from the heart 210, while maintaining sufficient lateral rigidity in the elongate arms 135 across the heart 210 when the elongate arms are deployed.

FIGS. 5-8 show a method of deploying the device 100 into a pericardial sack 200 in accordance with a first embodiment of the present invention. The device 100 is inserted into the pericardial sack 200 by dissecting just below the sternum 240 in a conventional manner. The device 100 is inserted into the pericardial sack 200 so that a distal end 102 of the device 100 is near an apex 211 of the heart 210. Typically, the medical practitioner holds the proximal end 101 of the device 100, which extends externally from the body. The proximal end 101 can be an extension of the trocar tube 115 or can be attached to some other medical instrument. The device 100 is generally hollow so as to allow various instruments to pass therethrough.

In practice, as shown in FIGS. 5-8, the elongate arms 135 are slowly deployed through the distal end 102 of the device 100 thereby forming a shape similar to an inverted umbrella 170. The inverted umbrella 170 can be deployed by inserting all of the elongate arms 135 into the device 100 and then pushing the elongate arms 135 out the distal end 102 of the device 100 at one time, or by separately inserting the elongate arms 135 into the proximal end 101 of the device and then pushing each elongate arm 135 in turn through the trocar tube 115 and out the distal end 102 of the device 100. In FIG. 6, the inverted umbrella 170 is partially deployed so that the elongate arms 135 are evident just beyond the distal end 102 of the device 100.

As seen in FIG. 7, the elongate arms 135 are then pushed further out from the device 100 so that the inverted umbrella 170 if further deployed and in contact with the surface of the heart 210. The tip portion 136 and first portion 135a of the elongate arms 135 are temporarily deflected further outward relative to the longitudinal axis of the device 100 as the elongate arms 135 initially contact the heart 210 in this manner. Thereafter, as deployment of the elongate arms 135 continues, the inwardly curved second portion 135b of the elongate arms 135 is deflected outward relative to the longitudinal axis of the device 100, which causes the tip portion 136 and first portion 135a of the elongate arms 135 to pull inwardly and maintain contact with the surface of the heart 210.

Referring still to FIG. 7, as deployment of the elongate arms continues further yet, the third portion 135c and fourth portion 135d of the elongate arms 135 act similarly to that described above with respect to the tip, first and second portions of the elongate arms 135 so as to maintain contact with the heart 210 even as deployment of the elongate arms 135 occurs. Finally, as seen in FIG. 8, the elongate arms 135 are fully deployed from the device 100, and are fully extended adjacent the heart 210 within the pericardial sack 200.

The device 100 is thus deployed by pushing the elongate arms 135 of the device 100 into the pericardial sack 200. The flexible qualities of the elongate arms 135 enable the arms to follow the curvature of the heart 210. On the other hand, the biased nature of the elongate arms 135 helps to maintain the inverted umbrella shape 170 of the elongate arms 135 even when the elongate arms 135 are fully deployed. The inverted umbrella 170 may be comprised of two or more elongate arms 135, as the skilled artisan should readily appreciate, although more than two elongate arms 135 are generally shown in the figures.

Figure 9:
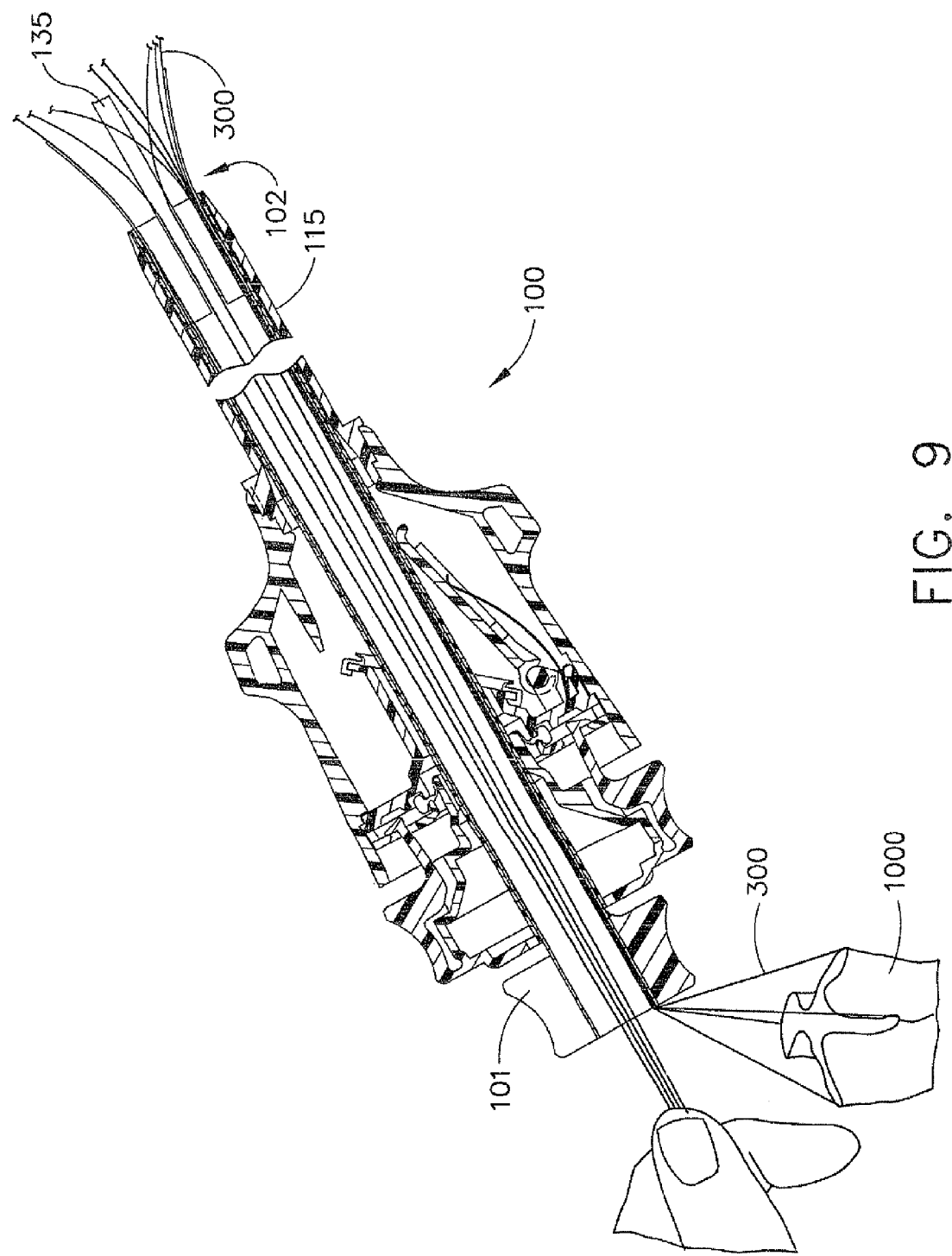

As shown in FIG. 9, the device 100 further comprises filaments 300 that have ends extending from the proximal end 101 of the device 100 for the medical practitioner to manipulate as desired. The filaments 300 connect to one or more of the elongate arms 135 at the distal end 102 of the device 100 and connect to a cardiac assist device, such as jacket 1000, at the proximal end 101 of the device 100, as will be described in greater detail below. One or more filaments 300 can be used. For example, one filament 300 can be used for every two elongate arms 135, or one filament 300 can be used for each elongate arm 135. The filaments 300 may comprise strings made of various materials, such as plastic, fiber or other biocompatible material such as bioabsorbable suture materials. The filaments 300 generally proceed through the trocar tube 115 and out the distal end 115b (102) thereof and return through the trocar tube 115 for connecting to the cardiac assist device, such as the jacket 1000, just beyond the proximal end 101 of the device 100. The cardiac assist device can be any type of wrapping means, such as the jacket 1000, which can be comprised of one of an elastic, plastic, or metal fibers.

Figure 10:
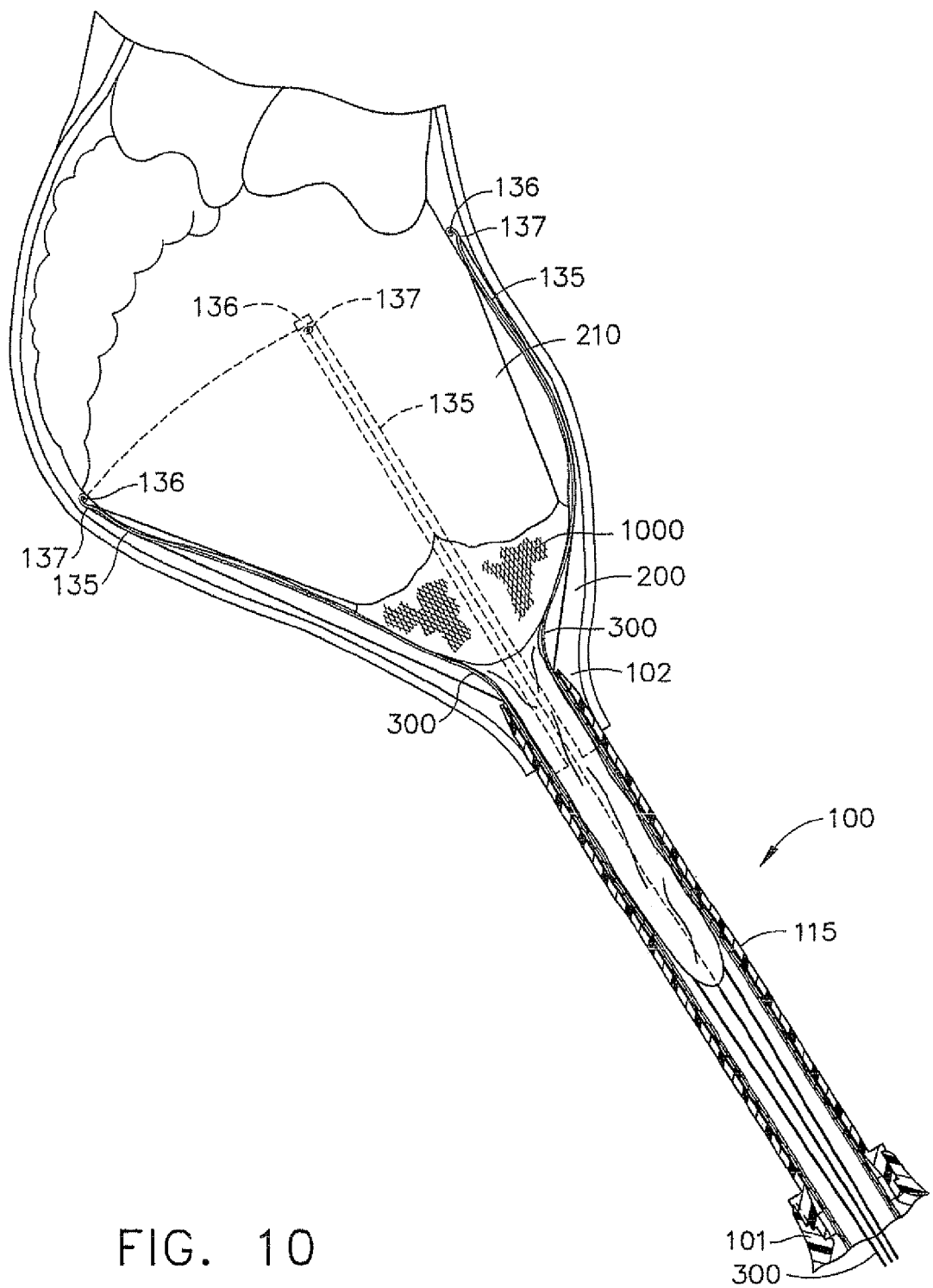

As seen in FIGS. 9 & 10, the filaments 300 proceed through the trocar tube 115 of the device and loop through an eyelet 137 provided at a distal end of each elongate arm 135, before returning through the trocar tube 115 and beyond the proximal end 101 of the device to connect to the jacket 1000. The filaments 300 may be attached to the elongate arms 135 through the eyelet 137 and to the jacket 1000 before the elongate arms 135 are deployed through the device 100 and into the pericardial sack 200 as shown. Alternatively, the filaments 300 may be pushed through the device 100 and eyelets 137, and attached to the jacket 1000 after the elongate arms 135 are deployed through the device 100. For convenience, the filaments 300 are attached to the elongate arms 135 through the eyelet 137, and to the jacket 1000 before the elongate arms are deployed through the device 100 as described herein. Manipulating the filaments 300 thus eventually positions the cardiac assist device, such as the jacket 1000, from a first position proximal the distal ends of the at least two elongate arms 135, to a second position about at least a portion of the heart 210. The jacket 1000 thus acts as a sub-pericardial sack to the heart 210 when fully positioned adjacent at least a portion of the heart according to the systems and methods of the invention.

Figure 11:
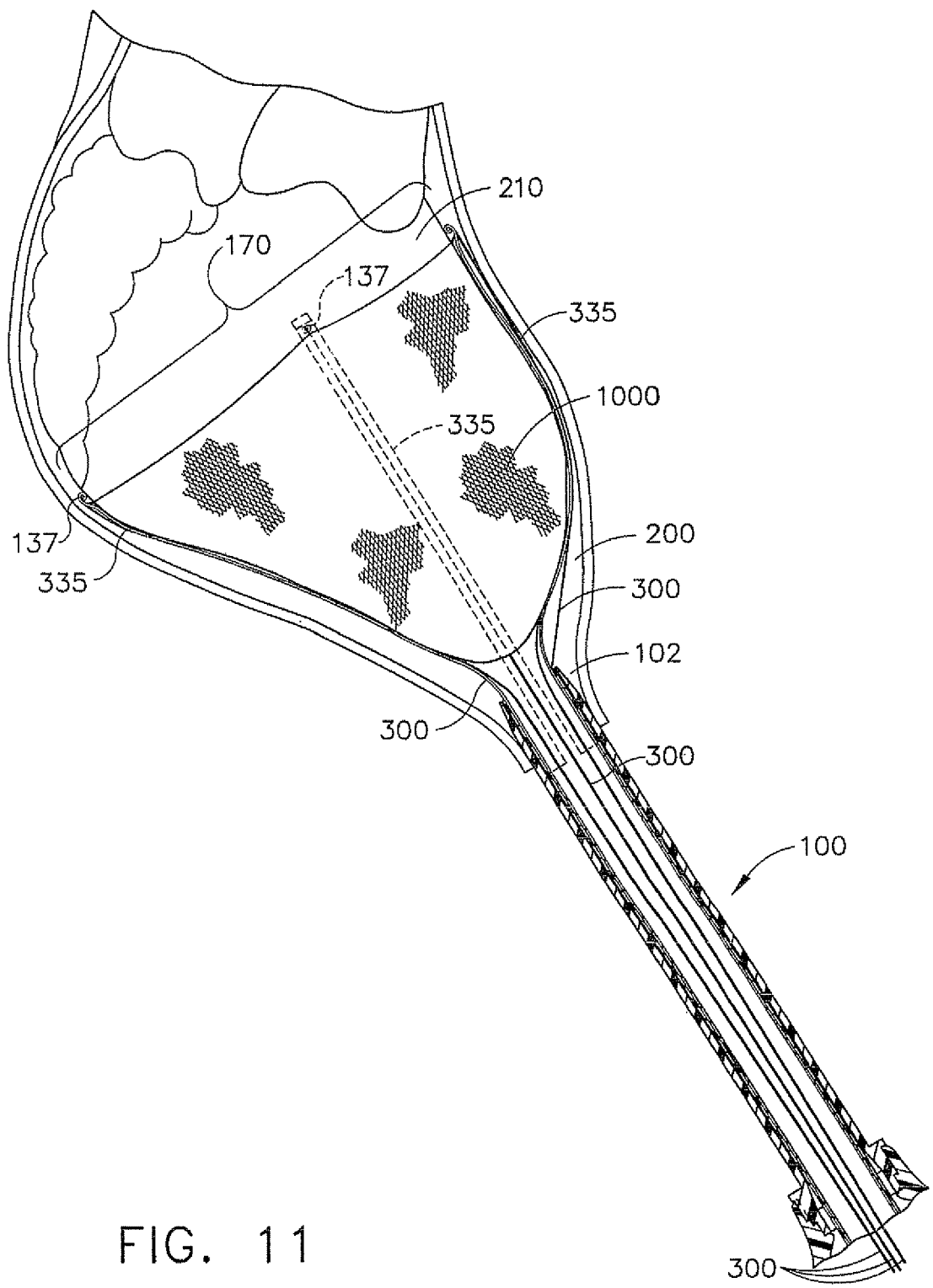

As shown in FIG. 11, once the elongate arms 135 and filaments 3000 are fully deployed in the pericardial sack 200, the filaments 300 of the device 100 are pulled by the medical practitioner to position the jacket 1000 even more closely about the heart 210. The medical practitioner pulls the filaments 300 until the jacket 1000 encloses the entire portion of the heart 210 as desired, as shown in FIG. 10. The naturally occurring beating of the heart 210 also aids in positioning the cardiac assist device, such as the jacket 1000, about the intended portion of the heart 210. The filaments 300 can also be used as a means to adjust and optimize tensioning of the jacket 1000 once the jacket is positioned as desired about the intended portion of the heart 210. Pulling of the filaments 300 tends to tighten the jacket 1000 even more once a desired position about the heart 210 is attained.

Referring still to FIG. 11, the inverted umbrella 170 is fully deployed within the pericardial sack 200. The elongated arms 135 each have an eyelet 137, respectively, to allow a filament 300 or tension wire to pass therethrough. As shown in FIG. 11, one filament 300 is used for each elongate arm 135. Each filament 300 thus enters through the proximal end 101 of the device 100, proceeds through the various components 110, 115, 120, 130 and 140 of the device 100 and out the distal end 102 of the device. Each filament 300 proceeds along a respective elongate arm 135 and through the eyelet 137, before returning through the various components to connect to the jacket 1000. Prior to pulling the filaments 300 therefore, the jacket 1000 (shown best in FIG. 10) is in an undeployed state in the dome of the inverted umbrella 170. In practice, each filament 300 is pulled at the proximal end 101 of the device 100 and through a corresponding one of the eyelets 137 at the distal end of the respective elongate arms 135 to cause the jacket 1000 to deploy, similarly to as a halyard and sail, to surround at least a portion of the heart 210. Once the jacket 1000 is positioned about the portions of the heart as desired, the jacket may be tightened around the heart 210 by further pulling of the filaments 300. Thereafter, any excess filament 300 may be cut-off and removed or left to degrade, as the filaments 300 are preferably made of a biodegradable material.

Of course, referring generally to FIG. 10 and the reference numerals therein, the artisan will readily appreciate that alternative embodiments of deploying the jacket 1000 can comprise connecting all of the filaments 300 at a proximal end thereof so that the user can hoist the jacket 1000 by pulling on the proximal ends of the connected filaments 300 at the proximal end 101 of the device 100. Still further, a single filament 300 spanning to connect at least two of the elongate arms 135 at the distal ends 136 thereof can be used (as shown in dashed lines). After positioning the at least two elongate arms 135 connected by the single filament adjacent at least a portion of the heart, then pulling or otherwise manipulating the single filament 300 hoists the jacket 1000 from an undeployed first position so as to at least partially deploy the jacket 1000 about at least a portion of the heart. Where provided, additional filaments 300 spanning to connect at least two other of the elongate arms 135 at the distal end thereof may also be used to help hoist the jacket 1000. Thereafter, further manipulation of the single filament, or additional filaments where provided, may be used exclusively or in combination with the natural rhythms of the heart to position the jacket 1000 as desired about the intended at least a portion of the heart. The distal tip of the at least two elongate arms 135 would preferably have a means to secure the cardiac assist device to the surface of the heart, and then disengage, allowing the at least two elongate arms to be retrieved at the conclusion of the deployment. A means to anchor and then release is described in FIG. 17. The cardiac assist device could also be secured through minimally invasive application of sutures or a surgical clip.

Referring again to FIGS. 5-8, for example, provides yet another alternative embodiment for deploying the jacket 1000 about the heart, whereby a single elongate arm 135 secures the jacket 1000 to a distal tip of the elongate arm. The arm 135 is deployed into the pericardial space and in contact with the surface of the heart as it is deployed. During deployment, the cardiac assist device would travel with the distal tip of the arm until the arm is fully deployed. The distal tip of the arm would preferably have a means to secure the cardiac assist device to the surface of the heart, and then disengage, allowing the elongate arm to be retrieved at the conclusion of the deployment. A means to anchor and then release is described in FIG. 17. The cardiac assist device could also be secured through minimally invasive application of sutures or a surgical clip. Once one edge of the cardiac assist device is in position, single or multiple additional elongate arms can be deployed. Once in position, a filament or filaments can be used to pull the remainder of the cardiac assist device into position. Of course, the natural rhythms of the heart can assist in the positioning of the cardiac assist device as well. Tensioning and securing the cardiac assist device would be accomplished as described above.

Figure 12:
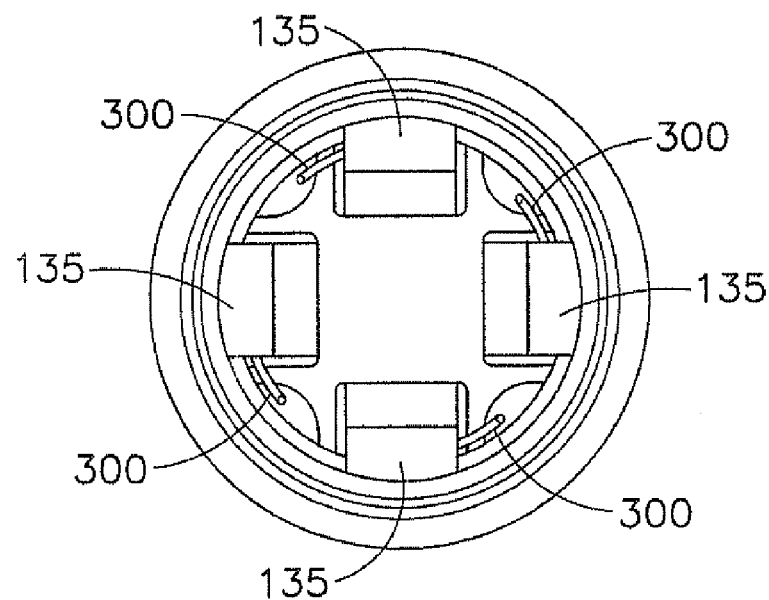
FIG. 12 illustrates a cross-sectional distal end view of filaments looped through eyelets of elongated arms of the device according to the systems and methods of the invention.
Figure 13:
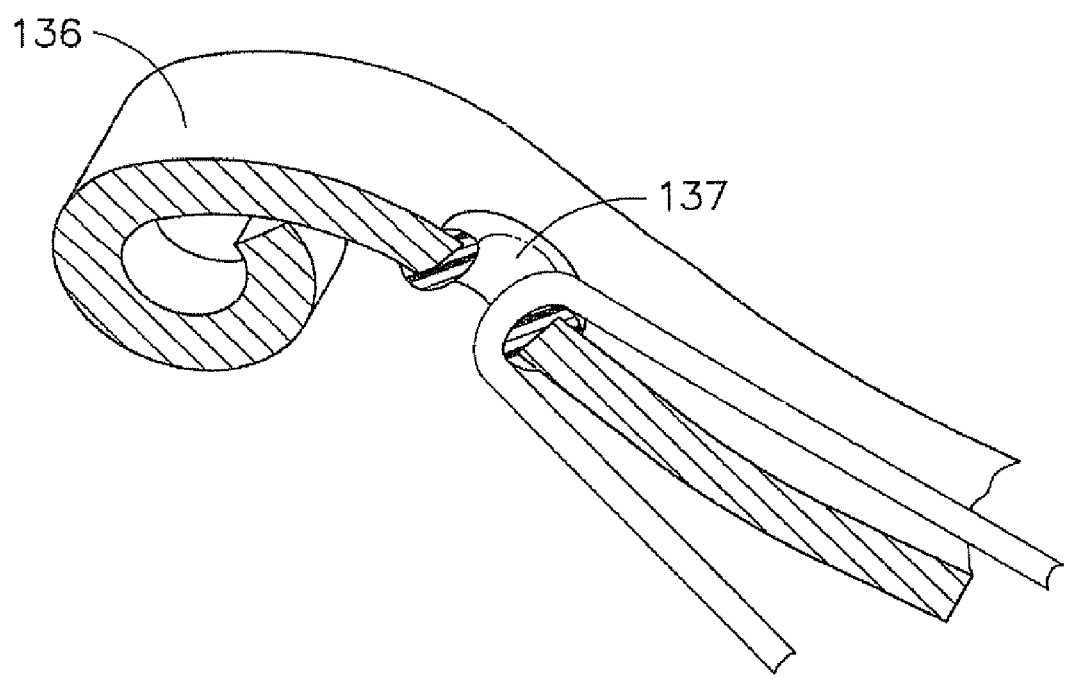
FIG. 13 illustrates a cross-sectional side view of an eyelet in an elongate arm according to the systems and methods of the invention.

FIG. 12 shows a distal end view of the device 100, whereby the filaments 300 extend through the eyelets 137 of the elongated arms 135. FIG. 13 shows in cross-sectional view, the eyelet 137 of an elongated arm 135 through which the filament 300 may loop. Of course, other means for holding the filaments 300 can be used instead of eyelets 137, such as different locations, shapes and forms that are capable of holding a filament for the same function. For example, the filament 300 could as easily be inserted through the open-looped tip 136 of the elongate arm 135 shown in FIG. 13, rather than through the eyelet 137.

Figure 14A:
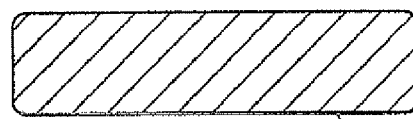
FIGS. 14a-14d illustrate cross-sectional view of other elongate arm configurations according to the systems and methods of the invention.
Figure 14B:
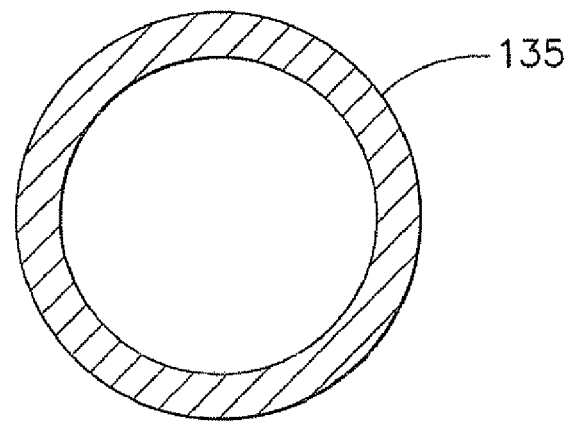
Figure 14C:
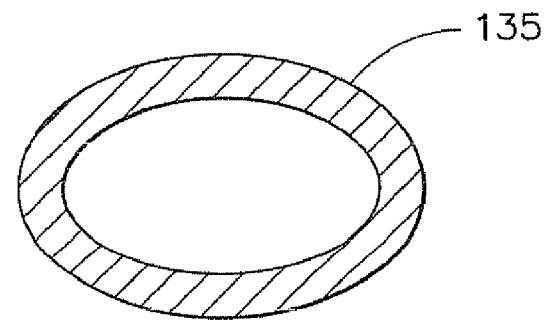
Figure 14D:
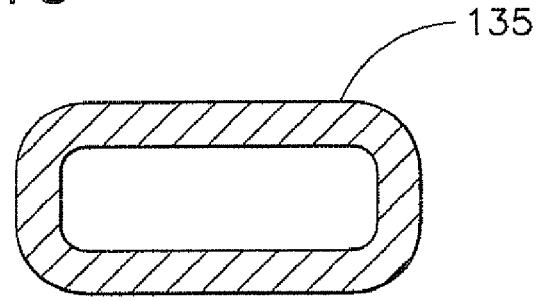

FIGS. 14(a)-14(d) show in cross-section, four other potential embodiments of the elongate arms 135 according to the systems and methods of the invention. FIG. 14a shows an elongate arm 135 comprised of a generally solid cross-section. FIG. 14b shows an elongate arm 135 comprised of a round/hollow cross-section. FIG. 14c shows an elongate arm 135 comprised of an oval/hollow cross-section. FIG. 14d shows an elongate arm 135 comprised of a generally rectangular/hollow cross-section. Of course, the artisan will readily appreciate that the eyelets 137 provided in any of the various embodiments of the elongate arm 135 shown in FIGS. 14a-d will generally comply with the description of the eyelets as described hereinabove.

Figure 15:
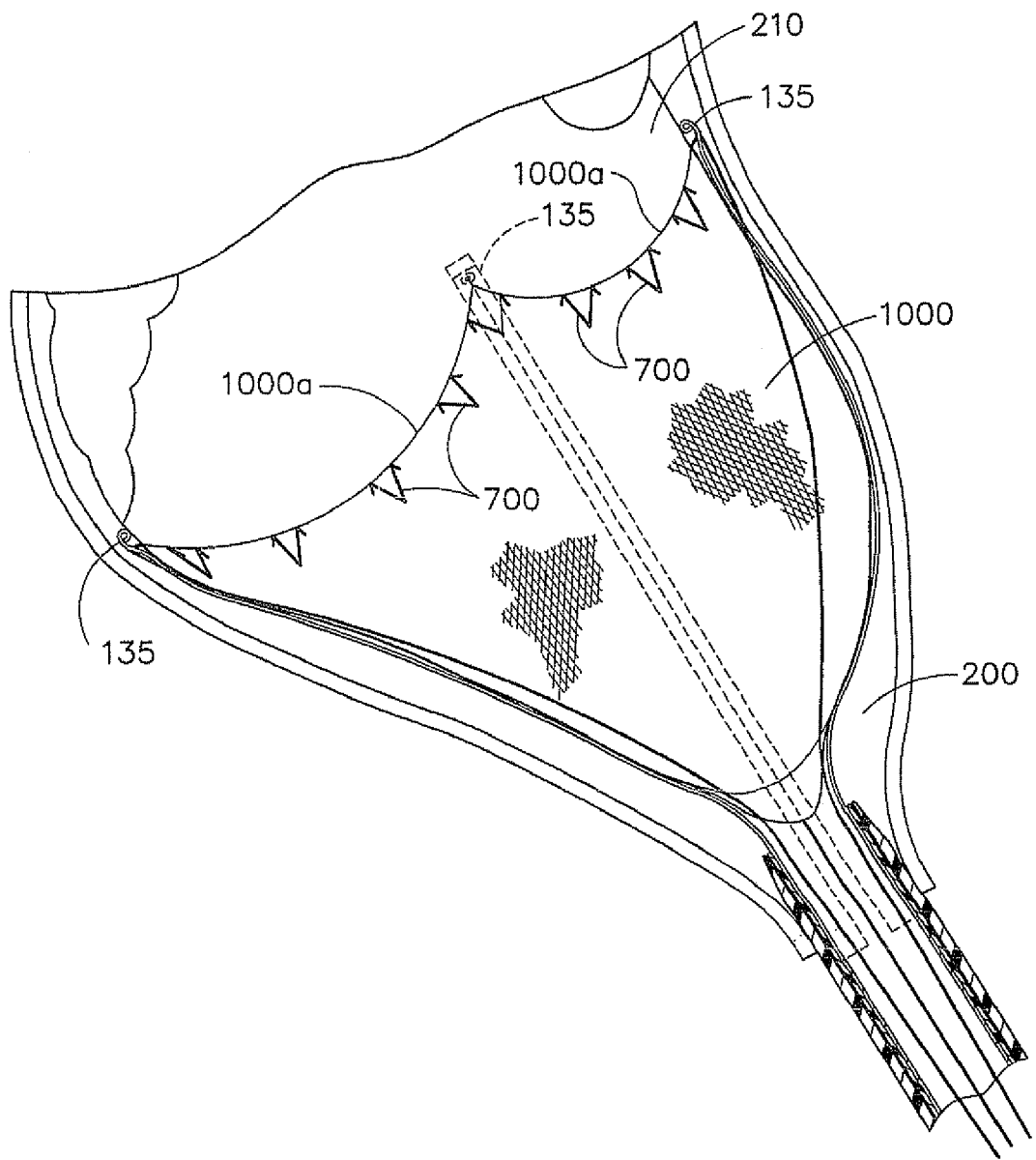
FIG. 15 illustrates a fully deployed cardiac assist device secured to the heart according to a first embodiment of the invention.

In some embodiments, the jacket 1000 gets tighter as the filaments 300 are pulled taught. The jacket 1000 is thus pulled until it covers a desired portion of the heart 210. The jacket 1000 can then be secured into position and either sutured to the heart 210 by providing one or more sutures or staples 700 along an upper end 1000a of the jacket 1000, as shown in FIG. 15, or the jacket 1000 can be otherwise secured to the heart via standard endoscopic techniques. Once the jacket 1000 is secured as desired about the intended portion of the heart 210, the elongated arms 135 can be retracted through the device 100 and removed from the pericardial space 200 through the access provided under the sternum 240. Thus, the invention provides a simpler and minimally invasive method for securing the jacket 1000 around intended portions of the heart 210 as compared to standard open sternotomy procedures.

Alternate methods can be used to secure the jacket 1000 to the heart 210 rather than using the filaments 300 once the jacket 1000 is positioned about the desired portion of the heart 210. Mechanical or suture based fastening via a second laparoscopic port, for example, could be used rather than using the same device 100 to fasten the jacket 1000. The fastener could be deployed through an opening in the pericardial sack 240, or directly through the pericardial sack 240 so that the pericardial sack 240 is fastened along with the cardiac assist device or jacket 1000 along the AV groove, for example. This alternative method may help facilitate an alternate, accurate tensioning of the jacket 1000 around the heart 210.

Once deployed as desired about intended portions of the heart, the jacket 1000 acts as a sub-pericardial sack, and is a cardiac assist device comprising a wrapping means made of a flexible, biocompatible material. The jacket 1000 is generally rectangularly shaped, but can also be generally tri-lateral or triangularly shaped. The skilled artisan should appreciate that any one of a variety of shapes may comprise the wrapping means of the jacket according to the invention provided sufficient material to fit and wrap the heart 210 closely is provided. Regardless of shape, it should be appreciated by a skilled artisan that the wrapping means may be any such type of plastic, elastic or metal fiber sheet known in the art for such cardio-surgical procedures as described herein, and does not have to be meshed, such as those described in copending U.S. patent applications Ser. Nos. 10/881,381, 10/881,511, and 10/881,510, all of which were filed Jun. 30, 2004 and are incorporated herein by reference.

The jacket or wrapping means 1000 may also be comprised of a shape-memory material. Shape-memory materials are stimuli-responsive materials, and have the capability of changing their shape upon application of an external stimulus. A change in shape caused by a change in temperature is called a thermally induced shape-memory effect. This shape-memory material would be deployed as a fabric for the jacket 1000 that once in position around the desired portion of the heart 210, would warm to body temperature and shrink to apply tension on the heart 210. The block copolymer composition of the shape memory material can be optimized to provide a slow response time, giving the medical practitioner enough time to position the jacket 1000, and provide correct shrinkage of the jacket 1000 for a snug fit around the heart 210.

Shape memory polymers that may be used are polyethylene-poly(vinyl acetate) block copolymers, radiation cross-linked polyethylene, polynorbornene, polyethers such as a combination of bisphenol A and propylene oxide, block copolymers made of polystyrene and poly(1,4-butadiene), block copolymers made of polyethylene terephthalate and polyethylene oxide, block copolymers made of oligo(ε-caprolactone)diol and oligo(p-dioxanone)diol, and block copolymers made of combinations of polyetherurethanes, polyesterurethanes, polyetherpolyesters, polyetherpolyamides, and others with polyether or polyester soft segments. Block copolymers of oligo(ε-caprolactone)diol and oligo(ρ-dioxanone)diol are of particular interest, which are the building blocks of resorbable suture material.

Many factors contribute to the successful deployment of the cardiac assist device, such as jacket 1000, into the pericardial sack 200 and about the heart 210. The fluids, regular motion and beat of the heart 210 within the pericardial sack 200 help the cardiac assist device to "float" into position about the heart 210 after deployment of the inverted umbrella 170 formed by the elongate arms 135 of the device 100. A fluoroscopic technique, as is known in the art, can be used to guide the device 100 under the sternum 240 and into the pericardial sack 200. Such fluoroscopic techniques can also be used to facilitate guiding the elongate arms 135 into a desired position about the heart 210. Also, an endoscope (not shown) can be inserted through the device 100, or through another opening or port provided in conventional manner through the pericardial space in close proximity to the dissecting access provided for the device 100, as will be appreciated by the skilled artisan.

Fluoroscopy is a radiologic technique in which a fluoroscope is used to visually examine the body or an organ. A fluoroscope utilizes an X-ray tube and fluorescent screen, with the area to be viewed placed between the screen and the tube. In this technique a portion of the body is exposed to a continuous beam of x-ray radiation to generate a movie like image that is viewed on a TV monitor. Fluoroscopy can thus be used by the operator of the present invention to assist accurate placement of the device 100, including the elongate arms 135 and inverted umbrella 170 and jacket 1000 within the pericardial sack 200 and about the heart 210. Fluoroscopy can also be used to avoid contacting the elongate arms 135 with the coronary vessels, and/or to minimize the likelihood of perforation of the coronary vessels or other tissues by the elongate arms 135 as they are deployed.

Figure 16:
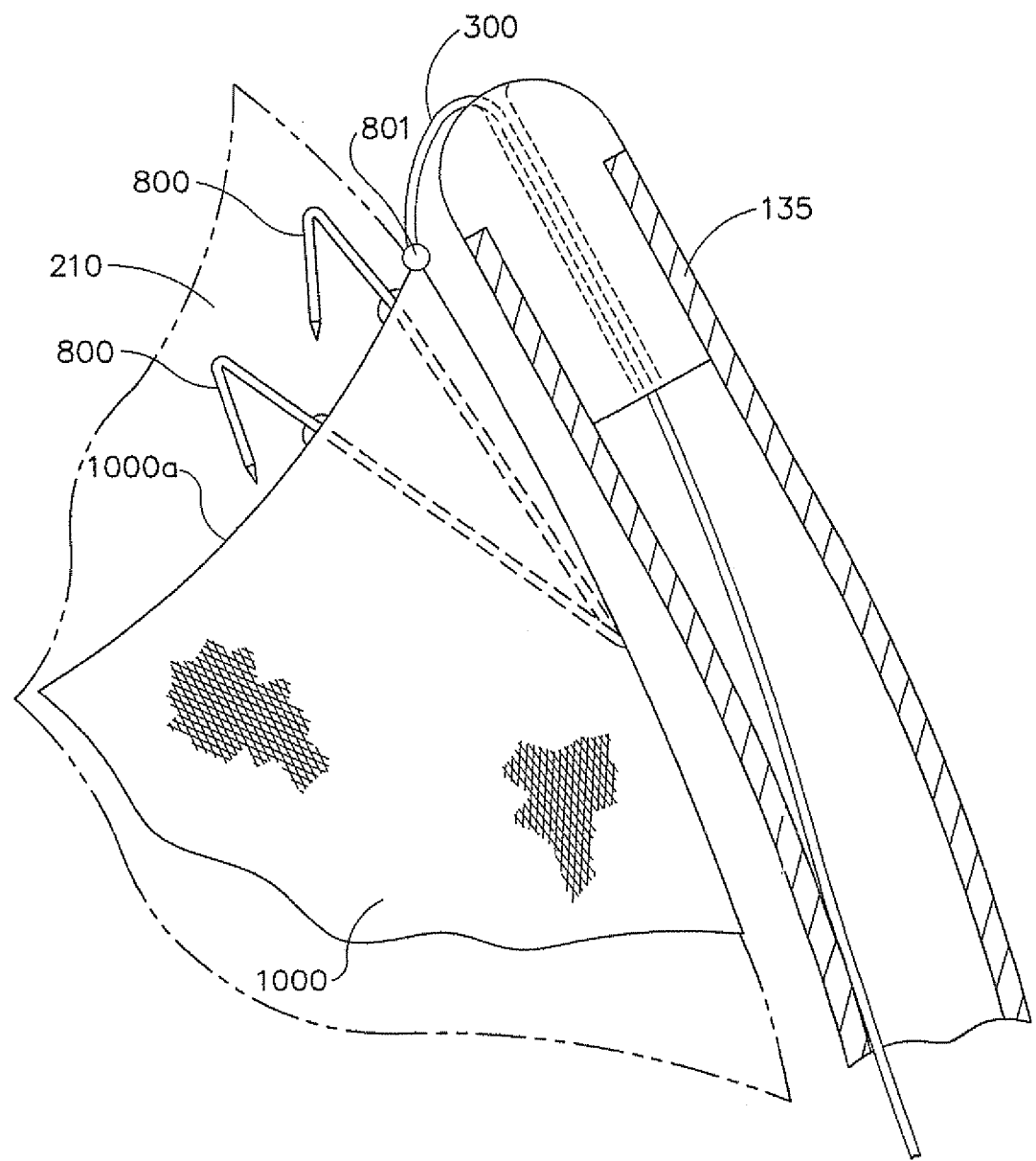
FIG. 16 illustrates another embodiment of deploying and securing a cardiac assist device to an intended portion of the heart according to the systems and methods of the invention.

In another embodiment of the systems and methods of the invention, as shown in FIG. 16, wherein components similar to prior described embodiments are generally omitted from duplicate description herein, the jacket 1000 can have one or more embedding hooks 800 and an attachment point 801 provided at various positions along the upper edge 1000a of the jacket 1000. The jacket 1000 is thus connected to the filaments 300 at attachment points 801. The hooks 800 secure the jacket 1000 to the heart 210 once the jacket 1000 has been positioned as desired about the intended portion of the heart 210. As long as the jacket 1000 is undergoing deployment by being pulled up and around the heart 210, the hooks (barbs) 800, due to their configuration, will not set; however, as soon as tension is released, the hooks 800 will set, thereby securing the jacket 1000 to the heart 210.

FIGS. 17a-17f illustrate another embodiment for deploying and securing a cardiac assist device to an intended portion of the heart, wherein components similar to prior described embodiments are omitted from duplicate description herein. As shown in FIGS. 17a-17f, one or more of the elongate arms 135 are provided with a hook 850. The hook 850 may be at the end of the respective elongate arm 135 distal from the eyelet 137 as seen in FIGS. 17a-17f. The hook 850 can be used to secure the jacket 1000 to the heart 210.

Figure 17C:
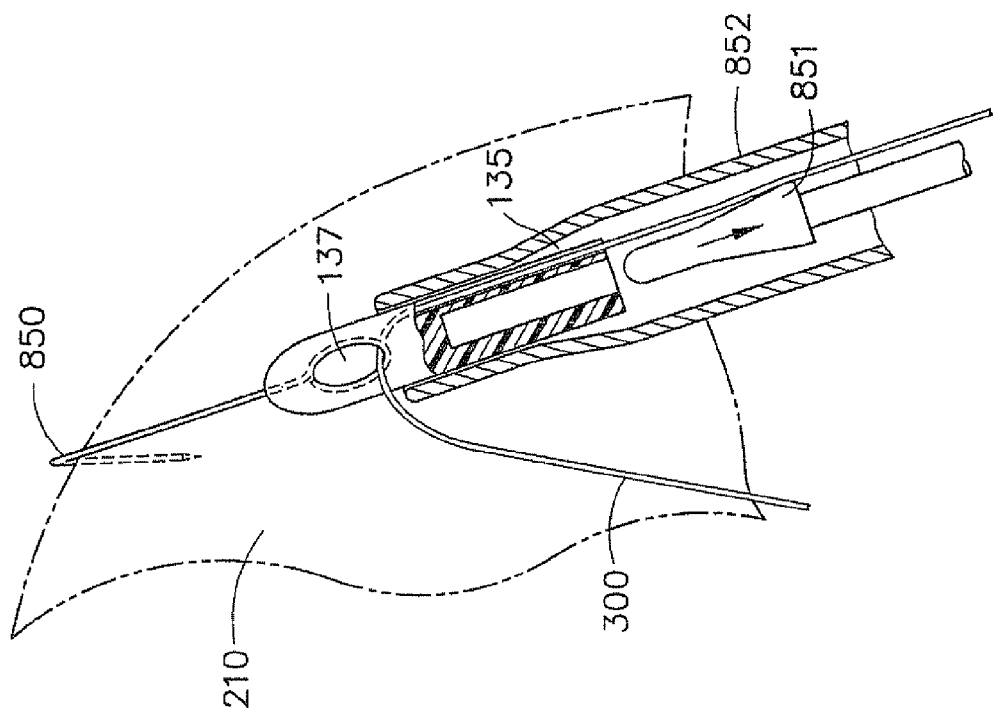
Figure 17D:
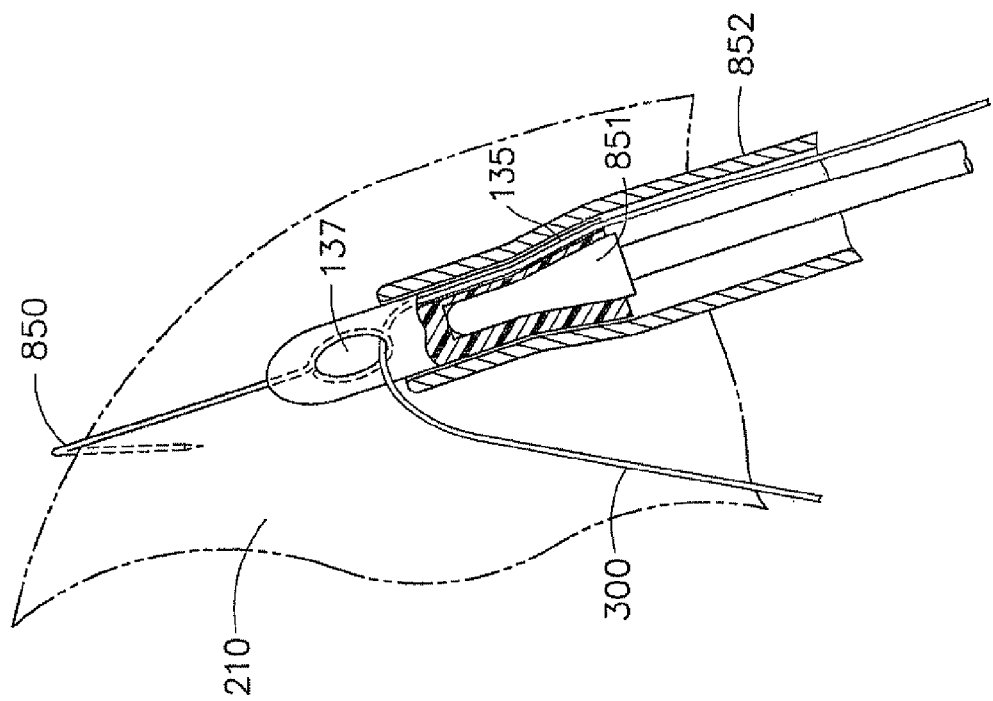

Referring to FIG. 17a, one or more of the elongate arms 135 can be hollow to allow use of an applicator 851. A protective sheath 852 can also be provided around the elongate arm 135 to prevent premature embedment of the hook 850 into the heart 210. In practice, once the jacket 1000 is positioned at the desired portion of the heart 210, the eyelet 137 is pushed out of the elongate arm 135 by the medical practitioner by pushing the applicator 851, as shown in FIG. 17b. The hook 850 is then embedded into a surface of the heart 210, as shown in FIG. 17c. As before, fluoroscopy can be utilized to ensure that the hooks 850 do not inadvertently deploy into the coronary vessels or other tissue as the elongate arms 135 and hooks 850 are deployed. The applicator 851 is then pulled out by the medical practitioner, as shown in FIG. 17d.

Figure 17F:
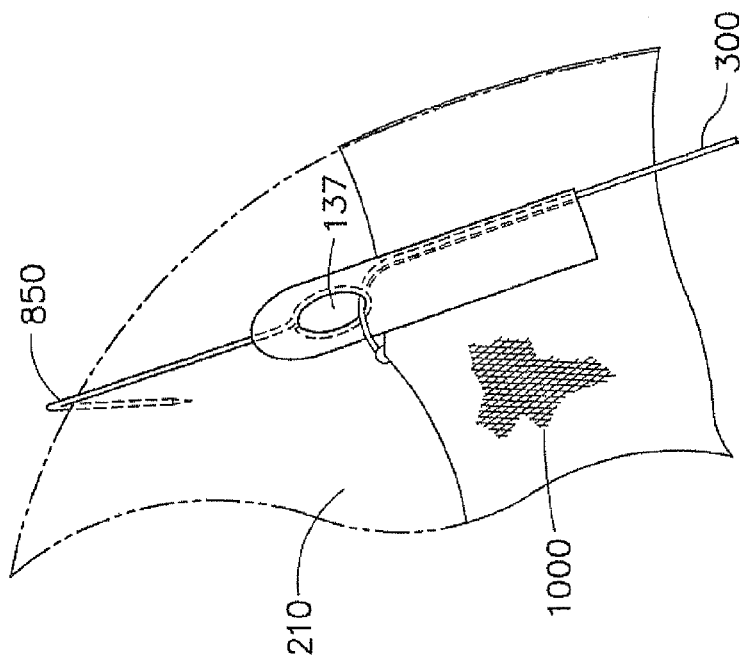
Figure 17E:
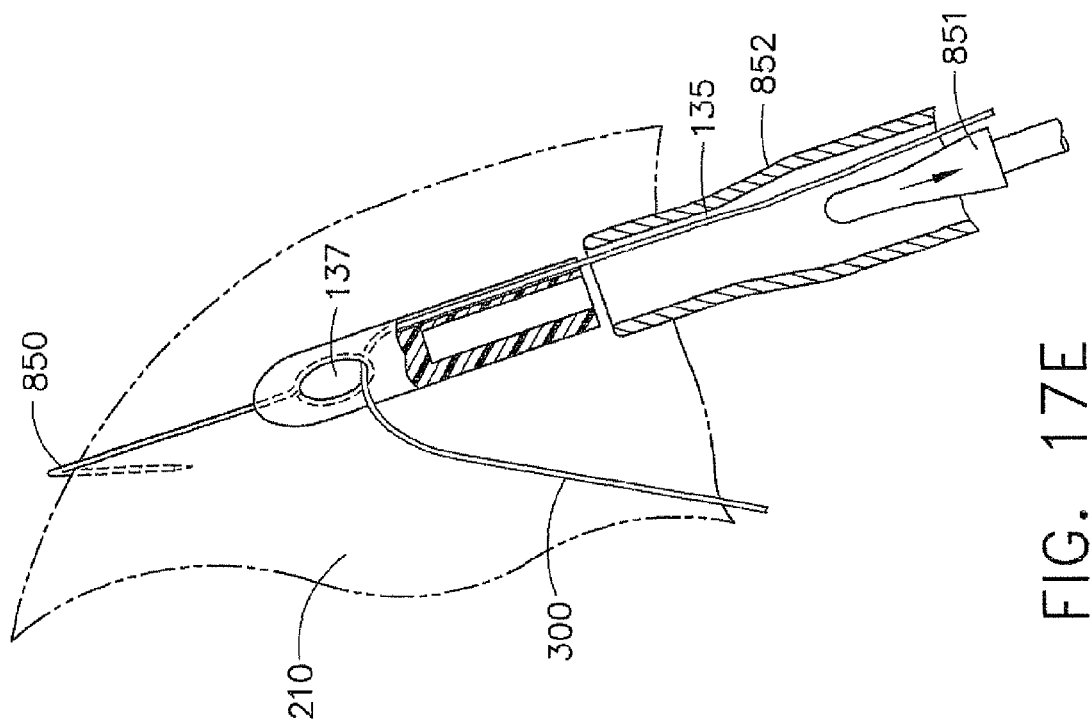

If traditional endoscopic procedures are used to secure the cardiac assist device 1000 to the heart, such as by stapling or suturing then the elongate arms 135 can be removed by retracting each arm through the medical device 100 as described above. However, the hook 850 on the elongate arms 135 can instead be separable therefrom, as shown in FIGS. 17e-17f. Where the hook 850 is separable, the elongate arms 135 may be retracted and removed from the pericardial sack 240 through the device 100 as before and the hook 850 can then be left behind to hold the jacket 1000 in place.

Referring still to FIGS. 17e & 17f, in particular, the eyelet 137 can also be left behind with the hook 850 in order to help hold the jacket or cardiac assist device 1000 in place and under tension, as shown in FIG. 17e. The filaments 300 are then tied, sutured, or otherwise secured in conventional manner to the eyelets 137 to hold the cardiac assist device 1000 in place and under tension, as shown in FIG. 17f. Securing the filaments 420 to the eyelets 430 may be done using known endoscopic techniques, for example, or other techniques known in the art. A knot pusher or other device known by the practitioner, may be used to secure the filaments 420 to the eyelet.

Figure 18:
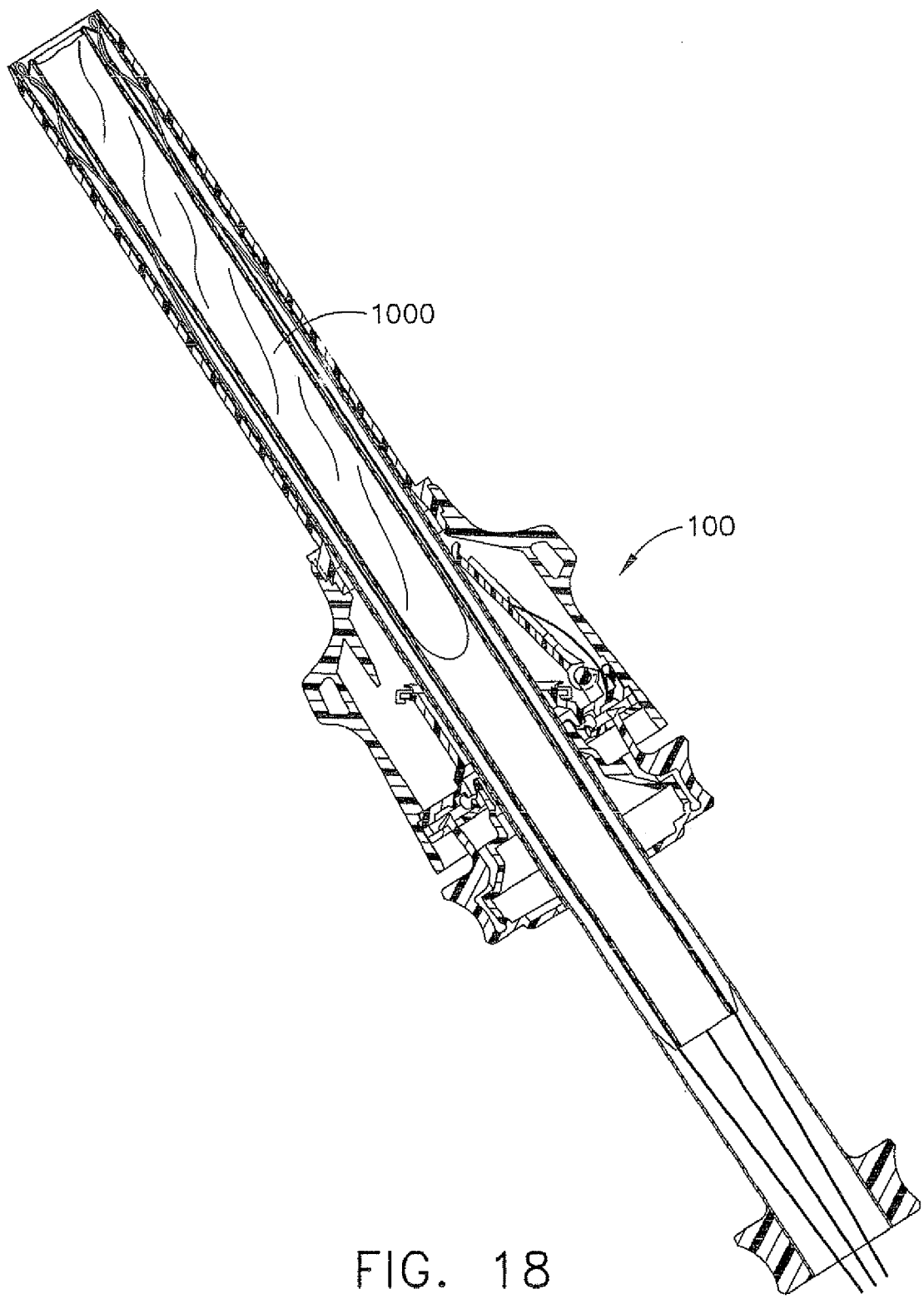
FIGS. 18-20 illustrate an alternative technique for deploying a cardiac assist device about an intended portion of the heart according to the systems and methods of the invention.
Figure 19:
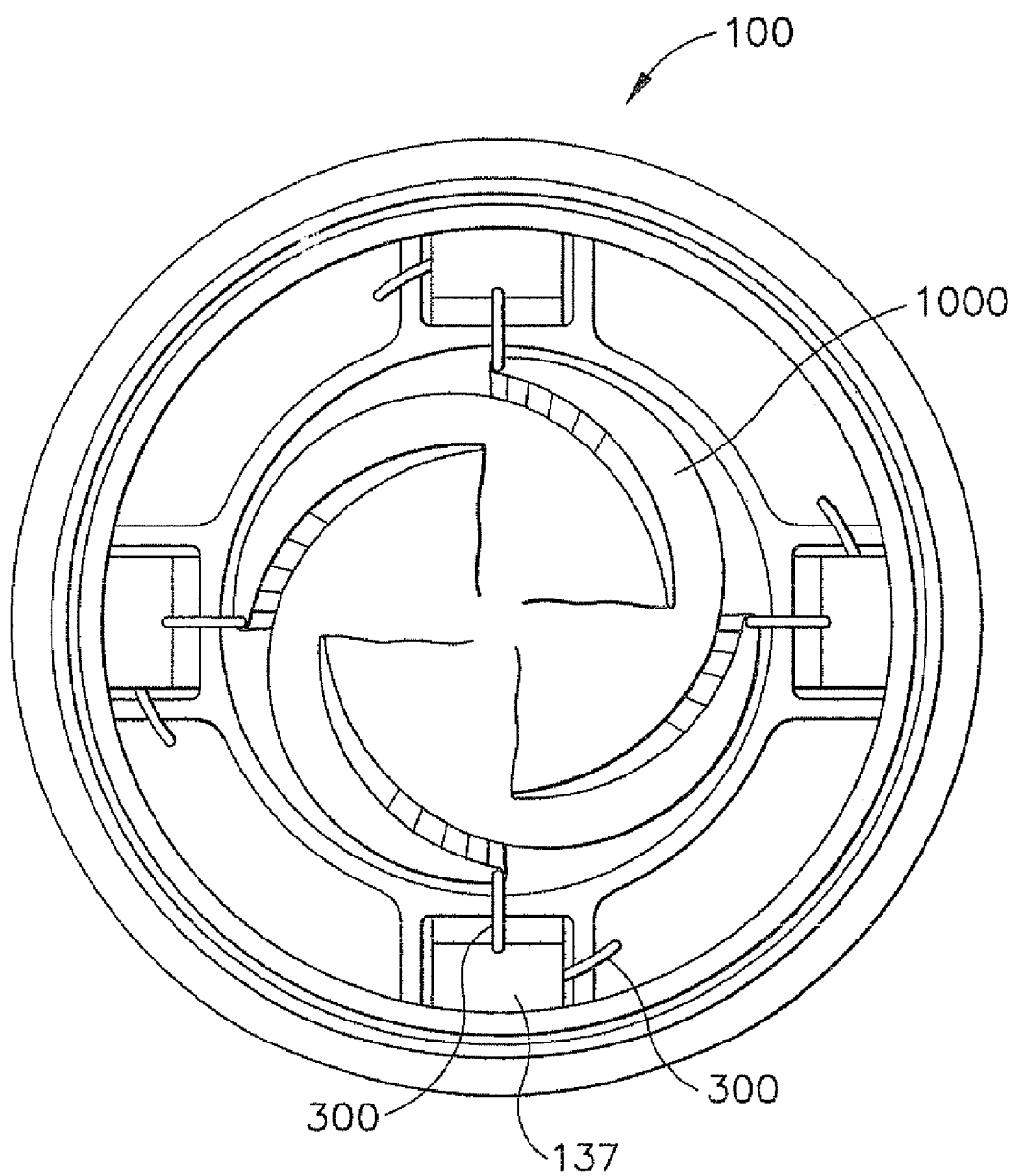
Figure 20:
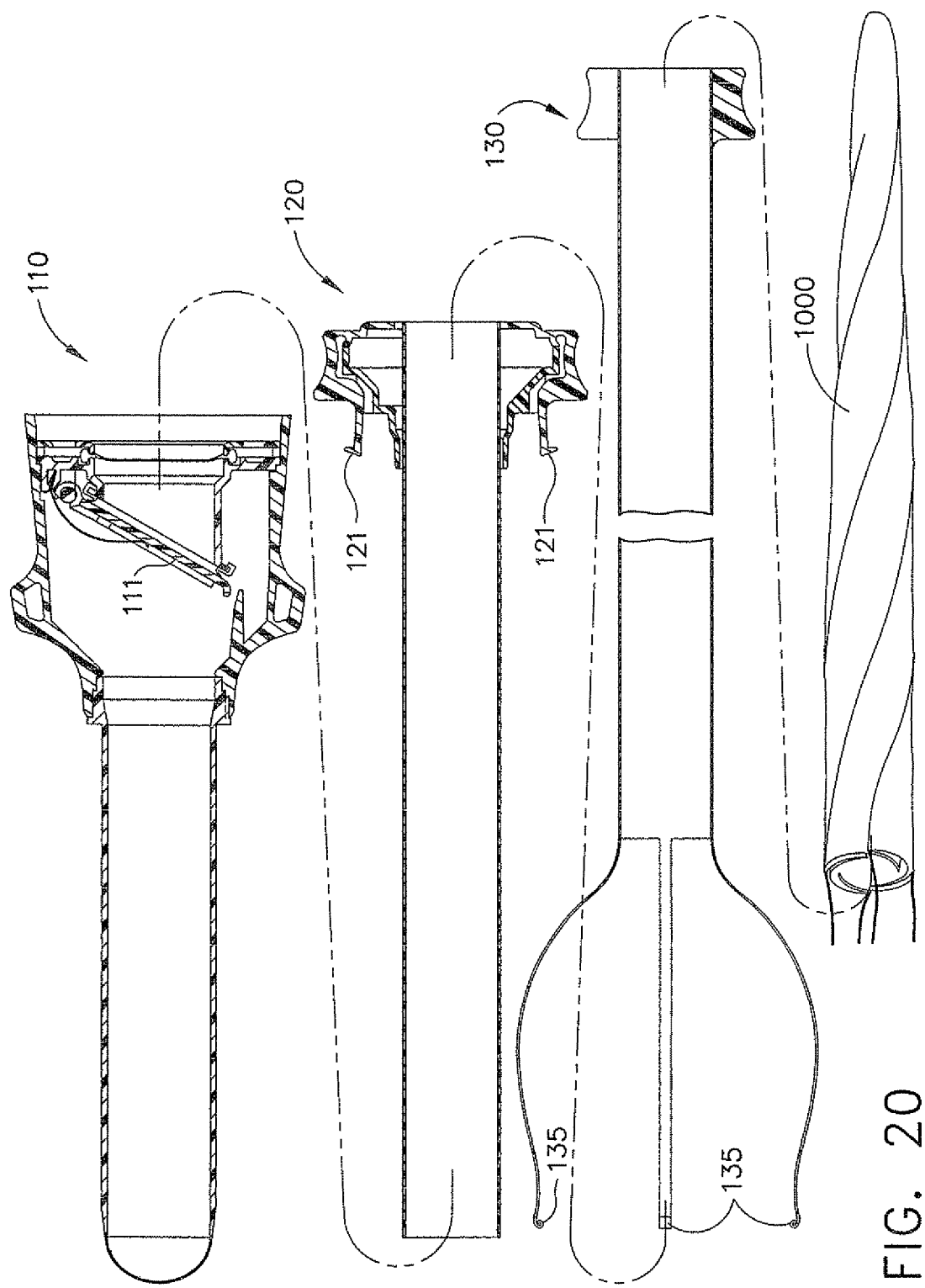

FIGS. 18-20 illustrate yet another alternative technique for delivering a cardiac assist device, such as jacket 1000, to an intended position about at least a portion of the heart 210 from a location other than adjacent the apex of the heart 210. Typically, the surgeon will establish access to the epicardium through sternotomy, thoracotomy, or less invasively, by thoracoscopic port access. In this technique, a large incision, or other opening such as that provided by a trocar tube, is made in a lateral side of the chest, usually in the region of the fifth intercostal space. One or more ribs may be removed from the patient, if medically determined advisable, and other ribs near the incision may be retracted outward to create an opening into the thoracic cavity, particularly where a non-trocar opening is used. In either case, the delivery device 100 may thus be inserted through the incision or opening into the pericardial sack 200. Once inserted, the delivery device proceeds downwardly along one side of the heart 210, around the apex 211 of the heart 210, and upwardly along the opposite side of the heart 210.

FIG. 18 shows an assembled view of the device 100 where the jacket 1000 is stored in an undeployed state within the device 100 prior to insertion of the device 100 into a patient. FIG. 19 shows a cross-sectional view at the distal end of the device 100 according to this embodiment, wherein the undeployed jacket 1000 is inside the device 100, and filament 300 are attached to the jacket 1000. The filaments 300 proceed through the eyelet 137 and before returning through the device to extend beyond the proximal end 101 thereof as in earlier embodiments. FIG. 20 is similar to the unassembled view of the device shown in FIG. 3(b), except that it shows the jacket 1000 inside the device 100.

FIGS. 21-25 show an alternative embodiment of a device and method for deploying a cardiac assist device 1000 adjacent a heart 210. The delivery device 900 includes like components as in prior described embodiments, wherein duplicate description of like components is generally omitted herein. The differences between the device 900 and the prior described embodiments are set forth below.

Figure 21:
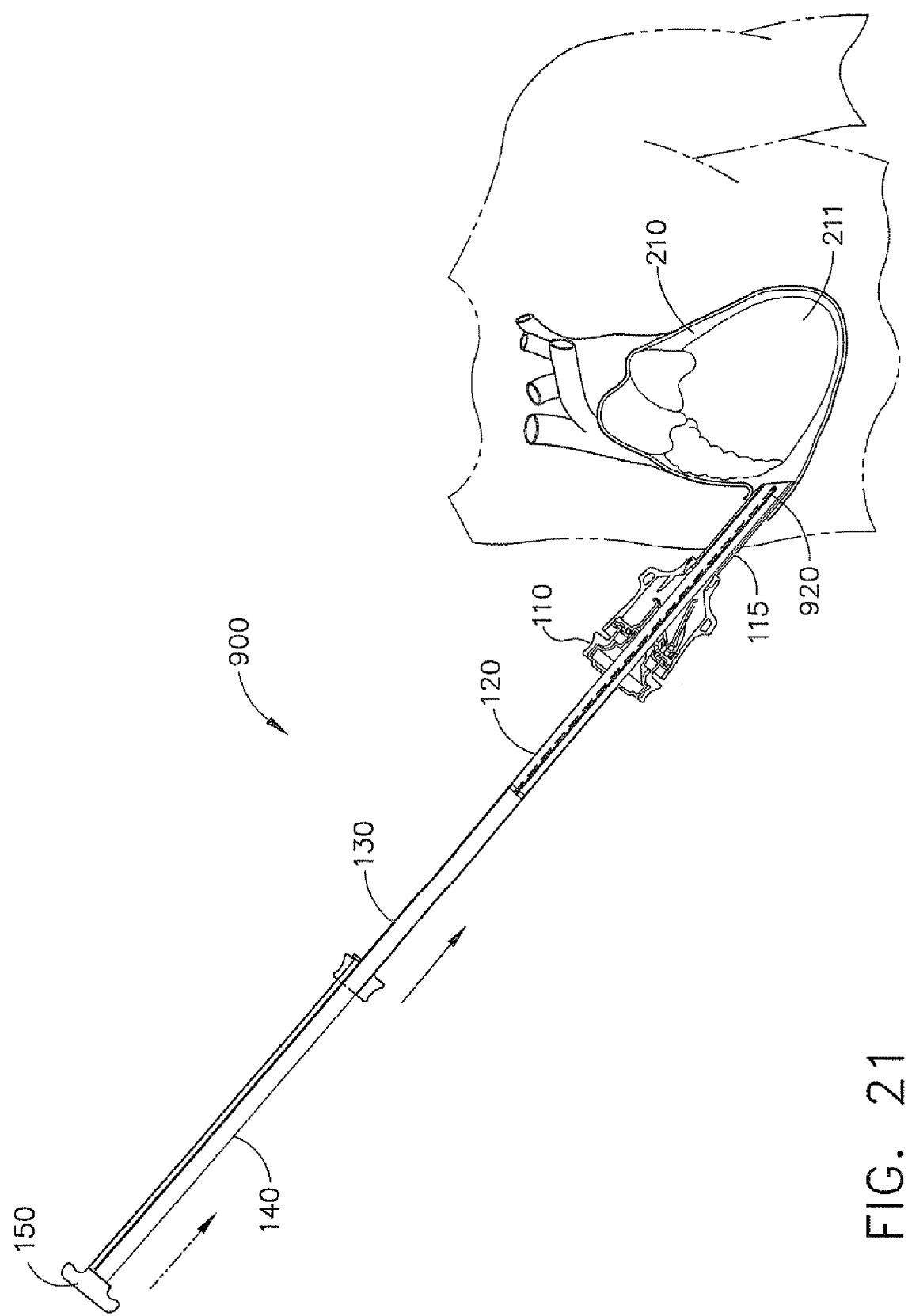
FIGS. 21-25 illustrate another embodiment of deploying and securing a cardiac assist device about an intended portion of the heart according to the systems and methods of the invention.
Figure 22:
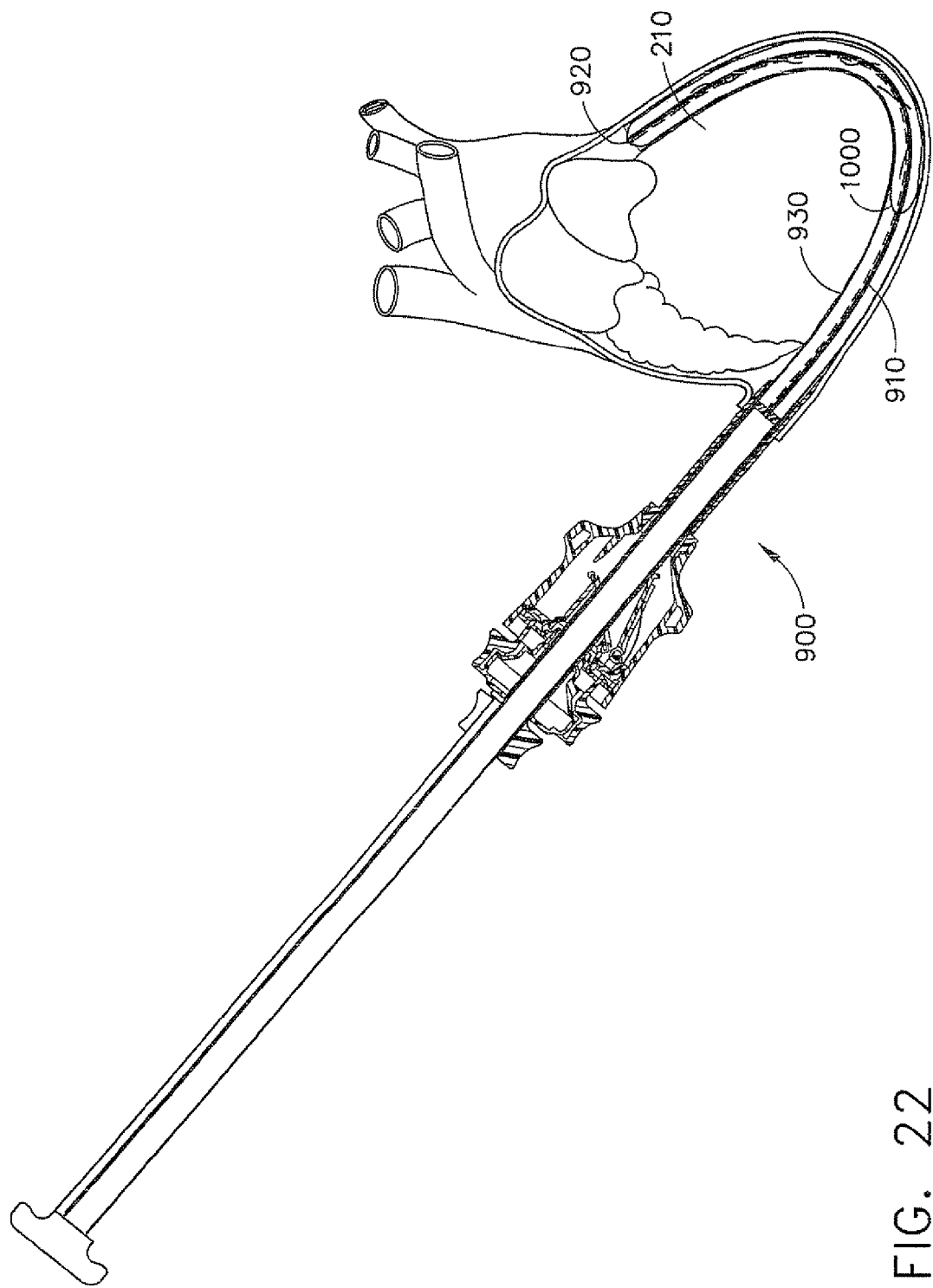

Referring to FIGS. 21 & 22, the delivery device 900 includes a steerable catheter 910 housed within the device 900. The steerable catheter 910 is deployed according to this embodiment rather than the elongate arms 135 of prior embodiments. The steerable catheter 910 includes steerable tip 920. Preferably, the steerable catheter 910 is further contained within a sheath 930. In practice, the steerable catheter 910 is preferably inserted through an opening or incision provided in the intercostals spaces proximate the heart 210. The steerable catheter 910 is then guided around the heart 210. As shown most clearly in FIG. 22, wherein the steerable catheter 910 of the device 900 is presumed to have entered the pericardial sack 240 through an opening or incision in the right intercostal space of a patient, the catheter 910 proceeds generally downwardly from its intercostal entry point and along the right ventricular side of the heart 210. The catheter 910 then proceeds further around the apex 211 of the heart 210 and then generally upwardly along the left ventricular side of the heart 210. As before, fluoroscopy can be used to help the medical practitioner guide the catheter 910 about the heart 210.

Figure 23:
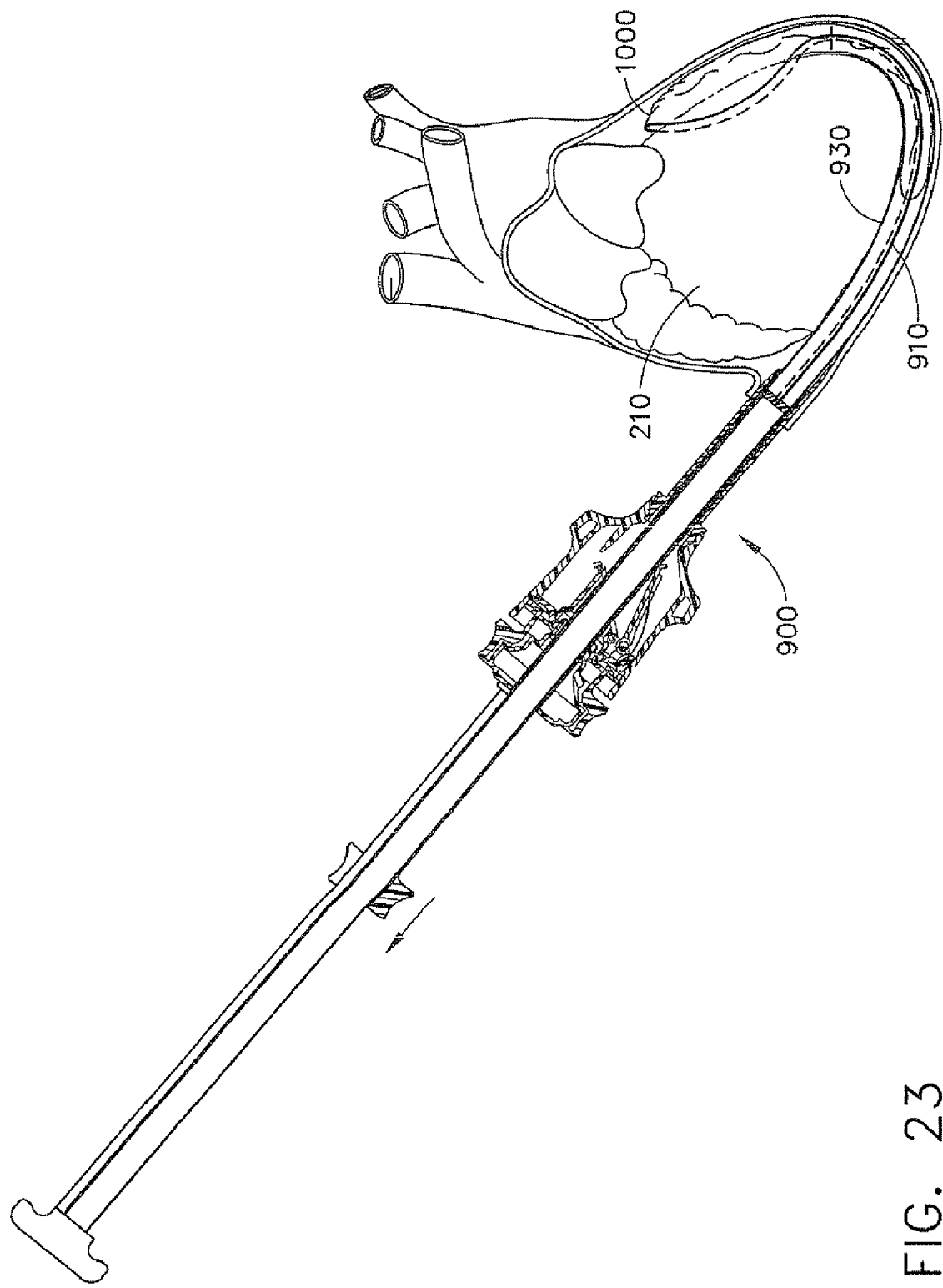
Figure 24:
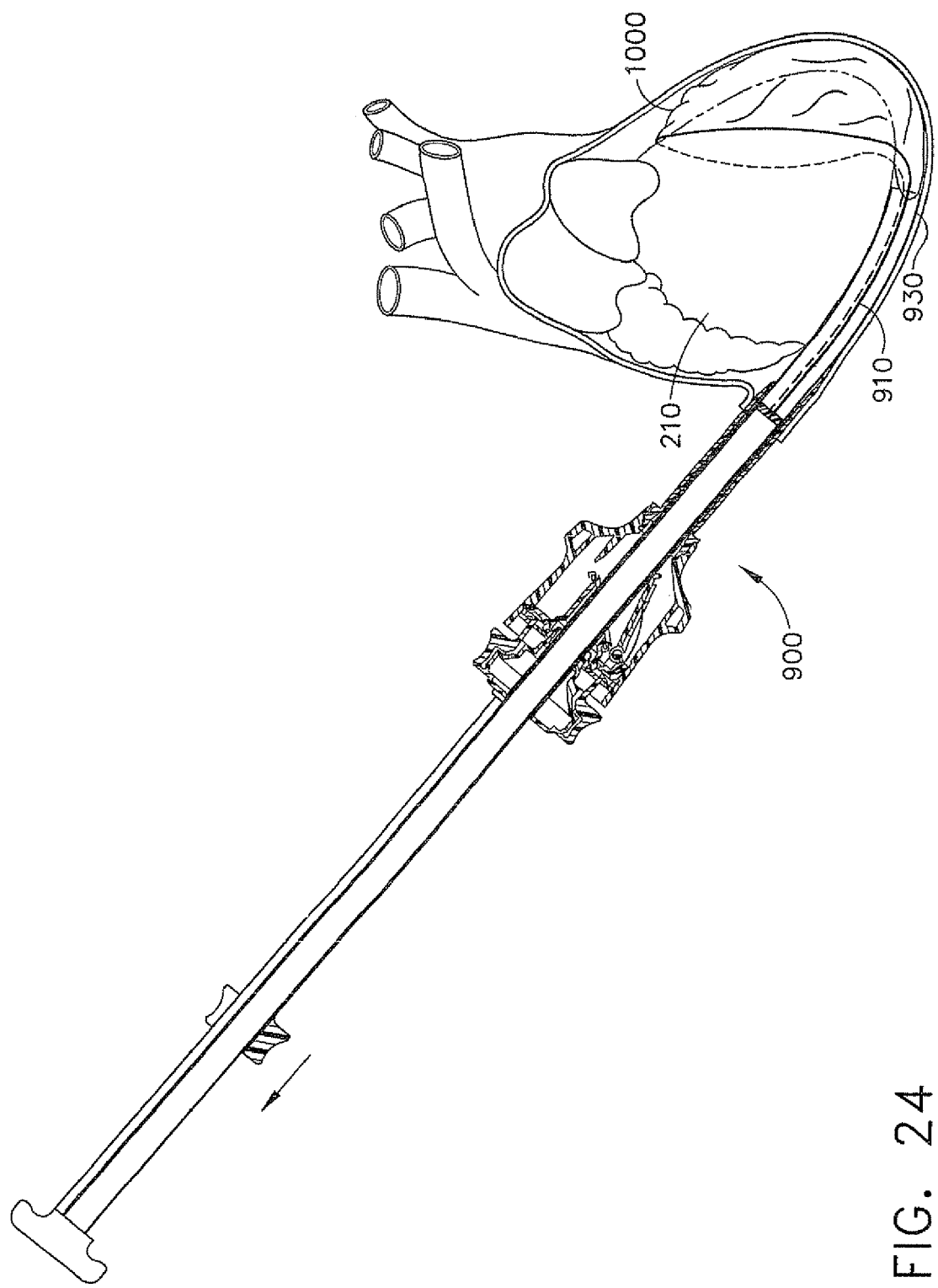
Figure 25:
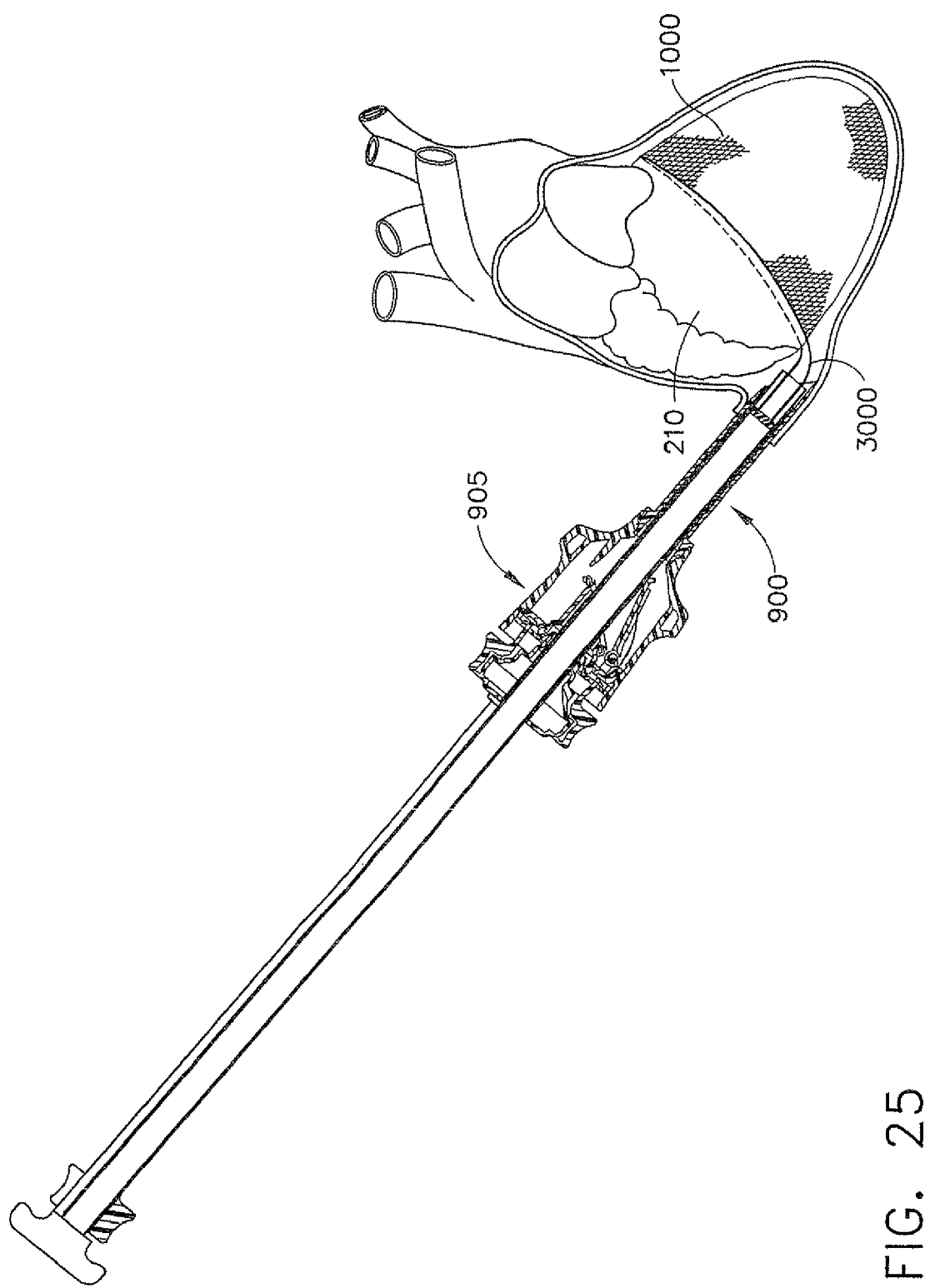

Referring now to FIG. 23, once the catheter 910 is positioned about the heart 210 similarly to as shown in FIG. 22, the sheath 930 is then pulled back through the device 900 to deploy the jacket 1000 originally housed within the sheath 930. Once the sheath 930 is pulled all the way back, the jacket 1000 is then positioned and placed around the heart 210, as shown in FIG. 24-25. Filaments 3000 are provided around and attached to the jacket 1000. The filaments 3000 extend from the jacket 1000 through the device 900 and out a proximal end 101 thereof for manipulation by the medical practitioner to adjust the tension of the jacket 1000 about at least a portion of the heart 210. Again, fluoroscopy can be used to help place and adjust the jacket 1000 about the heart 210. Thereafter, the jacket 1000 can be sutured, stapled, or otherwise anchored in the desired position about the heart 210 similar to as before, as should be appreciated by the artisan.

Figure 26:
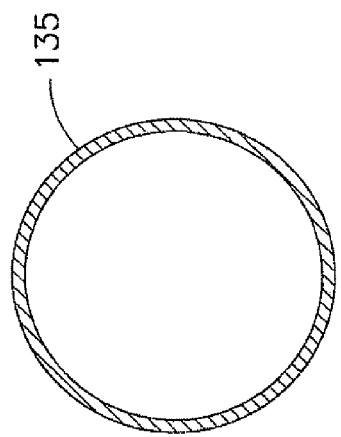
FIGS. 26-28 illustrate various alternative embodiments of the elongate arms according to the systems and methods of the invention.
Figure 27:
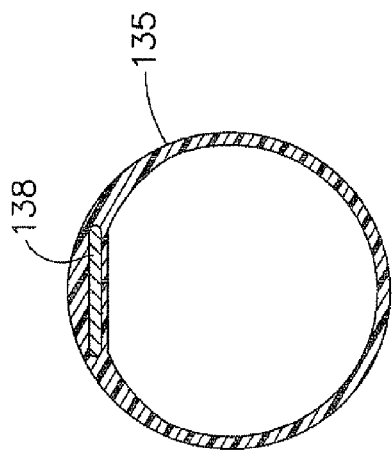
Figure 28:
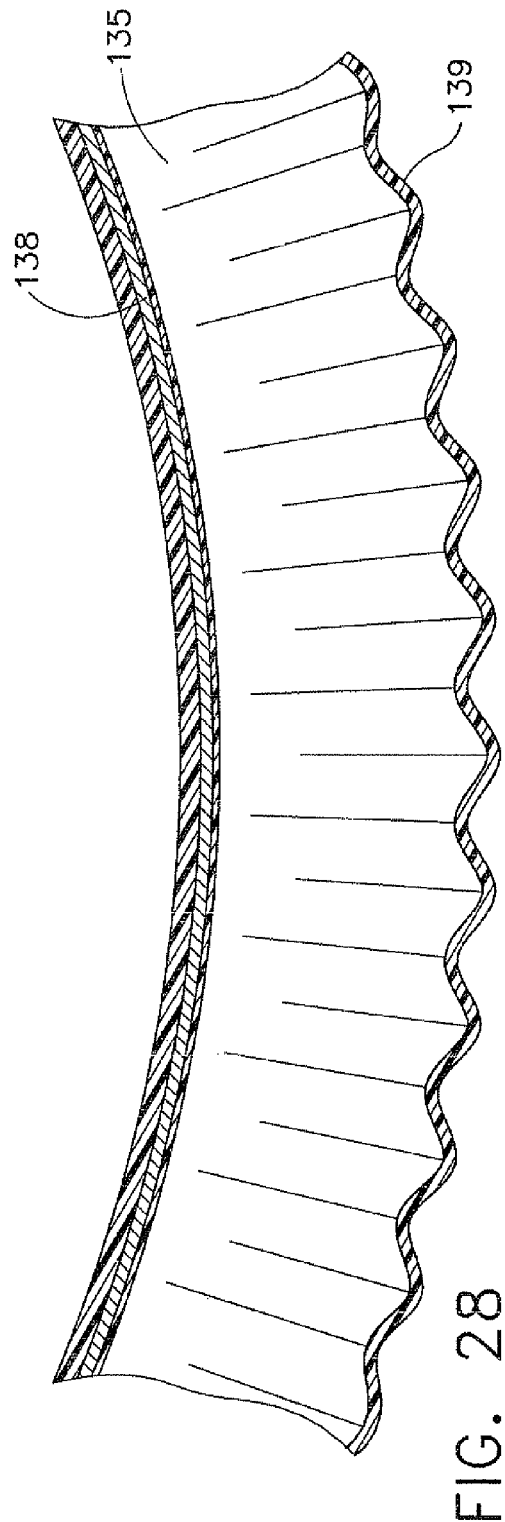

FIGS. 26-27 show various other alternate embodiments of the elongate arms 135 usable with appropriate embodiments of the systems and methods of the invention described herein. In FIG. 26, a generally hollow and circular elongate arm 135 is shown that is preferably made of a shape memory material. In FIG. 27, a generally hollow and at least semi-circular elongate arm 135 is shown with an internal biasing slat 138. The elongate arm 135 of FIG. 27 is preferably comprised of a biocompatible material such as a biocompatible polymer, whereas the biasing slat 138 of the elongate arm 135 of FIG. 27 is preferably comprised of the shape memory material. In FIG. 28, the shape memory material of the slat 138 opens to a desired shape, and a curtain 139 of the material gathers if the material is too large.

The various embodiments of the invention as described hereinabove are illustrative only and not intended to be limitations of the various aspects of the invention. Various other combinations of the present invention are possible, in which different types of medical devices may be used to deploy the umbrella or steerable catheter described above. Various devices other than the umbrella or steerable catheter may be used and deployed through the device described herein to provide a cardiac assist device adjacent the heart. Of course, where an open-chest technique is used a high degree of trauma, significant risk of complications, extended hospital stay, and a painful recovery period for the patient may be encountered. Accordingly, the less invasive techniques of deploying the jacket about desired portions of the heart are understood to be the preferred method of deploying the jacket according to the systems and methods of the invention.

Further, cardiac assist devices other than a mesh may be used in accordance with the invention. The cardiac assist devices can be of various shapes. The wrapping means as the cardiac assist device of the invention is not limited by the mesh sheet, and may comprise various other jackets and/or bags as would be known to one of ordinary skill in the art. Further, the wrapping means may be any type of flexible bio-compatible material including but not limited to plastic, elastic, or metal fiber known in the art as suitable for such procedures. The wrapping means is preferably made of a biologically compatible material. The skilled artisan will appreciate that the instruments described herein are exemplary only, and that various other arrangements are available without deviating from the spirit and scope of the invention.

While there has been shown and described what is considered to be preferred embodiments of the invention, it will, of course, be understood that various modifications and changes in form or detail could readily be made without departing from the spirit or scope of the invention. It is therefore intended that the invention be not limited to the exact forms described and illustrated herein, but should be construed to cover all modifications that may fall within the scope of the appended claims.

What is claimed is:

1. An apparatus for positioning a cardiac assist device adjacent at least a portion of a heart, the apparatus comprising:
   a hollow tubular instrument, the instrument having a proximal end and a distal end and a longitudinal axis; and
   at least two elongate arms movable from a first position within the instrument to a second position adjacent at least a portion of the heart;
   wherein each of said at least two elongate arms have a distal end comprised of a first portion curved outward relative to the longitudinal axis of the instrument; a second portion curved inward toward the longitudinal axis of the instrument; a third portion curved outward relative to the longitudinal axis of the instrument, and a fourth portion curved inward relative to the longitudinal axis of the instrument.

2. The apparatus for positioning a cardiac assist device of claim 1, wherein each of the at least two elongate arms have a lateral width portion across the heart greater than a thickness of a side portion towards the heart of each of the at least two elongate arms.

3. The apparatus for positioning a cardiac assist device of claim 1, wherein the distal end of each of the at least two elongate arms comprises a curled end.

4. A method for positioning a cardiac assist device adjacent at least a portion of a heart, the method comprising:
   creating an opening in the pericardium of a patient adjacent a ventricular side of the heart;
   inserting a delivery device into the opening;
   delivering a cardiac assist device through the delivery device into the pericardium; and
   disposing the cardiac assist device about at least a portion of the heart.

5. The method for positioning a cardiac assist device of claim 4, further comprising passing the delivery device through an intercostal space prior to the insertion step.

6. The method for positioning a cardiac assist device of claim 4, further comprising the step of inserting a steerable catheter having the cardiac assist device encased within a sheath through the delivery device.

7. The method for positioning a cardiac assist device of claim 6, further comprising:
   deploying a cardiac assist device adjacent the heart by pulling the sheath back.

* * * * *